United States Patent [19]

Deretic et al.

[11] Patent Number: 5,591,838

[45] Date of Patent: Jan. 7, 1997

[54] **DETECTION OF CONVERSION TO MUCOIDY IN *PSEUDOMONAS AERUGINOSA* INFECTING CYSTIC FIBROSIS PATIENTS**

[75] Inventors: Vojo Deretic; Daniel W. Martin, both of San Antonio, Tex.

[73] Assignee: Board of Regents, The University of Texas System, Austin, Tex.

[21] Appl. No.: 17,114

[22] Filed: Feb. 12, 1993

[51] Int. Cl.$^6$ .................................................. C07H 21/04
[52] U.S. Cl. ....................... 536/23.7; 536/24.32; 435/875
[58] Field of Search .......................... 435/252.34, 875; 536/23.7, 24.32

[56] References Cited

FOREIGN PATENT DOCUMENTS

WO86/07095  12/1986  WIPO .

OTHER PUBLICATIONS

Lamon–Fava et al., "Evolutionary distant mechanisms regulate apolipoprotein A–I gene expression: differences between avian and mammalian apoA–I gene transcription control regions", *Journal of Lipid Research*, 33(6):831–842, 1992.

Ikejiri et al., "The primary structure of the rat insulin–like growth factor II gene region", BBA Report—Short Sequence–Paper, *Biochimica et Biophysica Acta*, 1049(3):350–353, 1990.

Martin, D. W. et al., "Mechanism of Conversion to Mucoidy in *Pseudomonas aeruginosa* Infecting Cystic Fibrosis Patients," *Proc. Natl. Acad. Sci. USA*, 90:8377–8381, 1993, published in USA.

Martin, D. W. et al., "Differentiation of *Pseudomonas aeruginosa* into the Alginate–Producing Form; Inactivation of mucB Causes Conversion to Mucoidy," *Mol. Microbiol.*, 9(3):497–506, 1993, published in United Kingdom.

Deretic, V. et al., "Regulation of Muccoidy in *Pseudomonas aeruginosa*," to appear in the Oct., 1993 issue of *Bio/Technology*, published in USA.

Goldberg, Joanna B. et al., "A Mutation in algN permits trans Activation of Alginate Production by algT in Pseudomonas Species," *J. Bacteriol.*, 175(5):1303–1308, 1993, published in USA.

Goldberg, Joanna B. et al., "A Mutation in algN Permits trans Activation of Alginnate production by *algT in Psuedomonas Species,"J. Bacteriol.*, 175(5):1303–1308, 1993, published in USA.

Flynn, J. L. and Ohman, D. E."Cloning of Genes from Mucoid *Pseudomonas aeruginosa* Which Control Spontaneous Conversion to the Aliginate Production Phenotype," *J. Bacteriol.*, 170(4):1452–1460, 1988, published in USA.

(List continued on next page.)

*Primary Examiner*—Margaret Parr
*Assistant Examiner*—Scott Houttem
*Attorney, Agent, or Firm*—Arnold, White & Durkee

[57] ABSTRACT

Compositions and methods for detecting the conversion to mucoidy in *Pseudomonas aeruginosa* are disclosed. Chronic respiratory infections with mucoid *Pseudomonas aeruginosa* are the leading cause of high mortality and morbidity in cystic fibrosis. The initially colonizing strains are nonmucoid but in the cystic fibrosis lung they invariably convert into the mucoid form causing further disease deterioration and poor prognosis. The molecular basis of this conversion to mucoidy is also disclosed. The algU gene encodes a protein homologous to an alternative sigma factor regulating sporulation and other developmental processes in Bacillus, and along with the negative regulators mucA and mucB comprises the gene cluster controlling conversion to mucoidy. The switch from nonmucoid to mucoid state is caused by frameshift deletions and duplications in the second gene of the cluster, mucA. Inactivation of mucA results in constitutive expression of genes, such as algD, dependent on algU for transcription. Insertional inactivation of mucB on the chromosome of the standard genetic strain PAO also resulted in mucoid phenotype, and in a strong transcriptional activation of algD. Activation of algD results in increased synthesis of the exopolysaccharide alginate rendering *P. aeruginosaa* mucoid.

9 Claims, 25 Drawing Sheets

```
       425                              455
        |                                |
   AGCGAAGAGCAGGGGGCGCCGCAGGTGATCA

CAGGGGGCCAGGGGGC         OLIGO 568  (mucA2)

GAGCAGGG-GCGCC          OLIGO 578  (mucA22)

GAGCAGGGGGCGCCG         OLIGO 381  (mucA+)
```

OTHER PUBLICATIONS

Flynn, J. L. and Ohman, D. E. "Use of a Gene Replacement Cosmid Vector for Cloning Alginate Conversion Genes from Mucoid and Nonmucoid *Pseudomonas aeruginosa* Strains: *algS* Controls Expression of *algT*," *J. Bacteriol.*, 170(7):3228–3236, 1988, published in USA.

Martin et al., "Characterization of a Locus Detrmining the Mucoid Status of *Pseudomonas aeruginosa*: AlgU Shows Sequence Similarities with a Bacillus Sigma Factor," *Journal of Bacteriology*, 175(4), (galley proof copy) 1993, published in USA.

Govan et al., "Mucoid *Pseudomonas aeruginosa* and Cystic Fibrosis: The role of Mutations in Muc loci," *FEMS Microbiology Letters*, 100:323–330, 1992, published in Europe.

Deretic et al., "Muccid *Pseudomonas aeruginosa* and Cystic Fibrosis: Mutations in Muc Loci Affect Transcription of the algR and algD Genes in Response to Enviromental Stimuli," *Molecular Microbiology*, 4(2):189–196, 1990, published in United Kingdom.

Zielinski et al., "Alginate Synthesis in *Pseudomonas aeruginosa*: Enviromental Regulation of the algC Promoter," *Journal of Bacteriology*, 174(23):7680–7688, 1992, published in USA.

Konyecsni and Deretic, "DNA Sequence and expression Analsis of algP and algQ, Components of the Multigene System Transcriptionally Regulating Mucoidy on *Pseudomonas aeruginosa*: algP Contains Multiple Direct Repeats," *Journal of Bacteriology*, 172(5):2511–2520, 1980, published in USA.

Chitnis and Ohman, "Cloning of *Pseudomonas aeruginosa* algG, Which controls Alginate Structure," *Journal of Bacteriology*, 172(6):2894–2900, 1990, published in USA.

Goldberg and Dahnke, "Pseudomonas aeruginosa algB, Which Modulates the Expression of Alginate, Is a Member of the MtrC Subclass of Prokaryotic Regulators," *Molecular Microbiology*, 6(1);59–66, 1992 published in United Kingdom.

Dialog Search Report dated Feb. 4, 1993, printed in USA.

DNA database entry 544113 citing Lamon et al. J. Lipid Res. 33:831–842 (1992).

DMA database entry RN16F2 citing Ikejiri et al Biochim. Biophys Acta 1049:350–353, (1990).

DWA database entry N60554 citing WO86/07095 Dec. 4, 1986.

```
U4/76 (+)
GTCTATCTTG GCAAGACGAT TCGCTGGGAC GCTCGAAGCT CCTCCAGGTT CGAAGAGGAG    60
                                                            SD

M  L  T  Q  E  Q  D  Q  Q  L  V  E  R  V  Q  R  G  D  K
CTTTCATGCT AACCCAGGAA CAGGATCAGC AACTGGTTGA ACGGGTACAG CGCGGAGACA   120

R  A  F  D  L  L  V  L  K  Y  Q  H  K  I  L  G  L  I  V  R
AGCGGGCTTT CGATCTGCTG GTACTGAAAT ACCAGCACAA GATACTGGGA TTGATCGTGC   180

F  V  H  D  A  Q  E  A  Q  D  V  A  Q  E  A  F  I  K  A  Y
GGTTCGTGCA CGACGCCCAG GAAGCCCAGG ACGTAGCGCA GGAAGCCTTC ATCAAGGCAT   240

R  A  L  G  N  F  R  G  D  S  A  F  Y  T  W  L  Y  R  I  A
ACCGTGCGCT CGGCAATTTC CGCGGCGATA GTGCTTTTTA TACCTGGCTG TATCGGATCG   300
                                U4/33
                                 ┌──→  (-)
    I  N  T  A  K  N  H  L │ V  A  R  G  R  R  P  P  D  S  D  V
CCATCAACAC CGCGAAGAAC CACCTGGTCG CTCGCGGGCG TCGGCCACCG GACAGCGATG   360

T  A  E  D  A  E  F  F  E  G  D  H  A  L  K  D  I  E  S  P
TGACCGCAGA GGATGCGGAG TTCTTCGAGG GCGACCACGC CCTGAAGGAC ATCGAGTCGC   420

E  R  A  M  L  R  D  E  I  E  A  T  V  H  Q  T  I  Q  Q  L
CGGAACGGGC GATGTTGCGG GATGAGATCG AGGCCACCGT GCACCAGACC ATCCAGCAGT   480

P  E  D  L  R  T  A  L  T  L  R  E  F  E  G  L  S  Y  E  D
TGCCCGAGGA TTTGCGCACG GCCCTGACCC TGCGCGAGTT CGAAGGTTTG AGTTACGAAG   540

I  A  T  V  M  Q  C  P  V  G  T  V  R  S  R  I  F  R  A  R
ATATCGCCAC CGTGATGCAG TGTCCGGTGG GGACGGTACG GTCGCGGATC TTCCGCGCTC   600
EcoRV

E  A  I  D  K  A  L  Q  P  L  L  R  E  A
GTGAAGCAAT CGACAAAGCT CTGCAGCCTT TGTTGCGAGA AGCCTGA                  647
```

FIG. 6

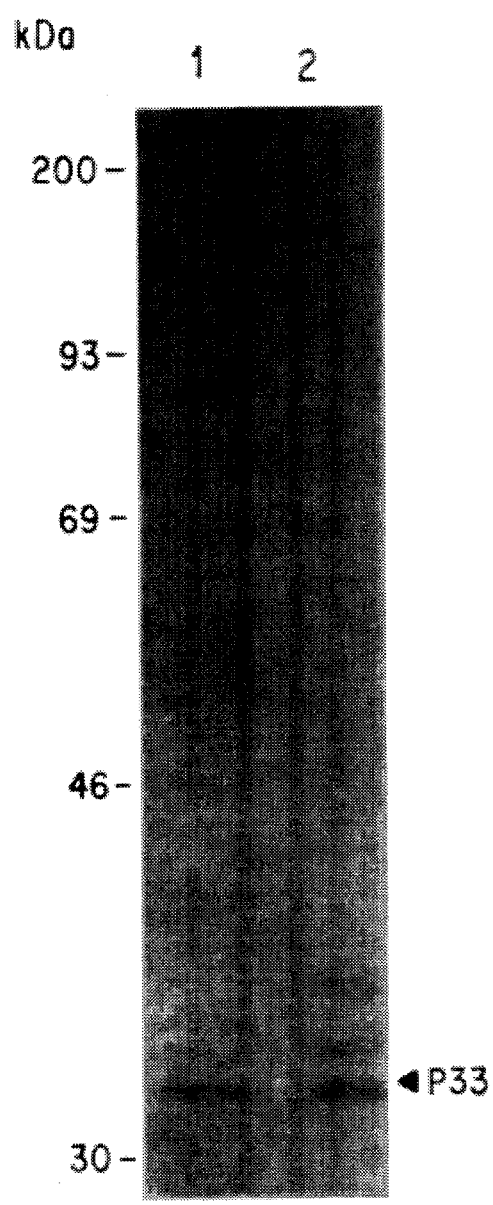
F I G. 8

```
                      algU                                          mucA
TTTGTTGCGA GAAGCCTGAC ACAGCGGCAA ATGCCAAGAG AGGTATCGCT ATGAGTCGTG      60
 L  L  R    E  A  *                            SD        M  S  R  E AAGCCCTGCA GGAAACTCTG TCCGCTGTGA TGGATAACGA AGCGGATGAA CTCGAGTTGC     120
 A  L  Q    E  T  L    S  A  V  M  D  N  E    A  D  E   L  E  L  R GGCGGGTGCT CGCAGCTTGC GGCGAGGATG CCGAGCTGCG TTCCACCTGG TCGCGTTACC     180
 R  V  L    A  A  C    G  E  D  A   E  L  R   S  T  W   S  R  Y  Q AGTTGGCGCG GTCCGTCATG CACCGCGAGC CTACCCTGCC GAAGCTGGAT ATCGCTGCGG     240
 L  A  R    S  V  M    H  R  E    P  T  L  P   K  L  D   I  A  A  A CGGTCTCTGC TGCCCTGGCC GACGAGGCCG CTCCGCCGAA AGCGGAGAAG GGACCGTGGG     300
 V  S  A    A  L  A    D  E  A  A   P  P  K    A  E  K   G  P  W  R GGATGGTCGG TCGCCTGGCG GTCGCTGCTC GGTGACCCTG GCGGTGCTGG CCGGCGTGCG     360
 M  V  G    R  L  A    V  A  A  S   V  T  L    A  V  L   A  G  V  R TCTGTACAAC CAGAACGACG CCCTGCCGCA AATGGCGCAA CAGGGGACCA CCCCGCAGAT     420
 L  Y  N    Q  N  D    A  L  P  Q   M  A  Q    Q  G  T   T  P  Q  I CGCCCTGCCT CAGGTGAAAG GCCCGGCCGT GCTGGCCGGC TACAGCGAAG AGCAGGGGGC     480
 A  L  P    Q  V  K    G  P  A  V   L  A  G    Y  S  E   E  Q  G  A GCCGCAGGTG ATCACCAACT CCTCGTCCAG CGATACCCGC TGGCATGAGC AGCGTCTGCC     540
 P  Q  V    I  T  N    S  S  S  S   D  T  R    W  H  E   Q  R  L  P CGATCTACCT GCGTCAGCAC GTGCAACAAT CCGCCGTCAG TGGTACAGAG AGCGCGCTGC     600
 I  Y  L    R  Q  H    V  Q  Q  S   A  V  S    G  T  E   S  A  L  P
```

FIG. 9A

```
                                                        mucB
CCTACGCTCG GGCAGCCAGC CTGGAAAACC GCTGAGGAGA GACATGCGCA CCACCTCCCT       660
  Y  A  R   A  A  S   L  E  N  R   *   SD         M  R  T   T  S  L GTTGCTTTTG CTTGGCAGCC TGATGGCGGT TCCCGCCACT CAGGCTGCCG ACGCTTCCGA       720
  L  L  L   L  G  S   L  M  A  V   P  A  T   Q  A  A   D  A  S  D CTGGCTGAAT CGTCTCGCCG AGGCCGATCG CCAGAACAGT TTCCAAGGCA CCTTCGTCTA       780
  W  L  N   R  L  A   E  A  D  R   Q  N  S   F  Q  G   T  F  V  Y BglII
CGAGCGCAAT GGCAGCTTCT CCACCCATGA GATCTGGCAT CGCGTGGAGA GCGATGGTGC       840
  E  R  N   G  S  F   S  T  H  E   I  W  H   R  V  E   S  D  G  A GGTTCGCGAG CGCCTGCTCC AGCTCGACGG CGCGCGCCAG GAAGTGGTCC GGGTCGACGG       900
  V  R  E   R  L  L   Q  L  D  G   A  R  Q   E  V  V   R  V  D  G GCGCACCCAG TGCATCAGCG GCGGCCTTGC CGACCAACTG GCCGATGCCC AGCTGTGGCC       960
  R  T  Q   C  I  S   G  G  L  A   D  Q  L   A  D  A   Q  L  W  P GGTGCGCAAG TTCGATCCCT CCCAGCTGGC TTCCTGGTAC GACCTGCGCC TGGTCGGGGA      1020
  V  R  K   F  D  P   S  Q  L  A   S  W  Y   D  L  R   L  V  G  E ATCCCGTGTC GCCGGCCGCC CGGCAGTGGT CCTTGCGGTG ACTCCGCGCG ACCAGCATCG      1080
  S  R  V   A  G  R   P  A  V  V   L  A  V   T  P  R   D  Q  H  R CTACGGCTTC GAGCTGCACC TGGACCGCGA CACCGGCCTG CCGTTGAAGT CGCTGCTGCT      1140
  Y  G  F   E  L  H   L  D  R  D   T  G  L   P  L  K   S  L  L  L GAACGAGAAG GGGCAGTTGC TCGAGCGCTT CCAGTTCACC CAGTTGAATA CCGGCGCGGC      1200
  N  E  K   G  Q  L   L  E  R  F   Q  F  T   Q  L  N   T  G  A  A
```

FIG. 9B

```
ACCTGCCGAA GACCAGTTGC AGGCGGGCGC CGAATGCCAG GTCGTCGGCC CGGCCAAGGC    1260
  P  A  E   D  Q  L    A  G  A    E  C  Q    V  V  G  P    A  K  A

CGACGGGGAG AAGACCGTGG CCTGGCGCTC GGAATGGCTG CCGCCAGGTT TCACCCTGAC    1320
  D  G  E   K  T  V    A  W  R  S  E  W  L    P  P  G  F    T  L  T

┌─ΔUM9  *
          ───┘│
CCGCAGTTTC ATGCGTCGCA GTCCGGTCAC CCCCGATCCG GTCGCCTGCC TGACCTATGG    1380
  R  S  F   M  R  R  S  P  V  T    P  D  P    V  A  C  L    T  Y  G

CGATGGCCTG GCACGATTCT CGGTGTTCAT CGAGCCGCTG CACGGTGCCA TGGTTGGCGA    1440
  D  G  L   A  R  F  S  V  F  I    E  P  L    H  G  A  M    V  G  D

CGCGCGCAGC CAGCTCGGCC CGACCGTGGT GGTTTCCAAG CGCCTGCAGA CCGATGACGG    1500
  A  R  S   Q  L  G  P    T  V  V    V  S  K    R  L  Q  T    D  D  G

CGGCCAGATG GTGACCGTCG TCGGCGAAGT GCCGCTGGGC ACCGCCGAGC GGGTGGCGCT    1560
  G  Q  M   V  T  V  V    G  E  V    P  L  G    T  A  E  R    V  A  L

GTCCATCCGG CCCGAGGCCG CCGCCCAGAA ATGATCGAGG AGCAGGGGCG AGTGGTGGCG    1620
  S  I  R   P  E  A  A    A  Q  K    *

ACCGAGCCGG GAGCGGTATG GGTCGAGACC GTGCGCCGAG TACCTGCTCG TCCTGCTCGG    1680

CCAATGCCGG TTGCGGCCAG GGGCTGATGC AGCGCCTGGG CGTCGGCGCG GGGCGTGCCC    1740

EcoRI
GGGTGCGCGC GTTGAGCGAC CTGAGCCTGC GGGTCGGCGA TGCGGTCGTC CTAGGAATTC    1800
```

```
       425                                    455
        |                                      |
AGCCGAAGAGCAGGGG GCGCCCGCAGGTGATCA
         CAGGGGC CAGGGGC           OLIGO 568  (mucA2)
       GAGCAGGG-GCGCC              OLIGO 578  (mucA22)
       GAGCAGGGG GCGCCG             OLIGO 381  (mucA+)
```

FIG. 12B

```
     360                          390
      |                            |
AACAGGGGACC A CCCCGCAGATCGCC
      GGGACC-CCCCGCA            OLIGO CF1
      GGGACC A CCCCGC            OLIGO 365/377
```

AGGTATCGCTATGAGTCGTGAAGCCCTGCAGGAAACTCTGTCCGCTGTGATGGATAAC
<u>SD</u>      M  S  R  E  A  L  Q  E  T  L  S  A  V  M  D  N

GGCGAGGATGCCGAGCTGCGTTCCACCTGGTCGCGTTACCAGTTGGCGCGTCCGTCA
 G  E  D  A  E  L  R  S  T  W  S  R  Y  Q  L  A  R  S  V  M

CGGTCTCTGCCCTGCGACGAGGCCCCGAAAGCCGAAGGACCGTG
 V  S  A  A  L  A  D  E  A  P  P  K  A  E  K  G  P  W

GGCGGGTGCTGGCCGGCGTGCGCGTCTGTACAACCAGATGGCG
 A  V  L  A  G  V  R  L  Y  N  Q  N  D  A  L  P  Q  M  A
                                    mucA2       Δ(mucA22 CF14 CF23)

GGCCCCGGCGTTGCTGGCCGGCTACAGCGAAGAGCAGGGCGCGCCAGCTGATCACCA
 G  P  A  V  L  A  G  Y  S  E  E  Q  G  A  P  Q  V  I  T  N
                                                    Bcl I

CGATCTACCTGCGTCAGCACGTGCAACAATCCGCCGTCAGTGGTACAGAGAGCGCGCT
 I  Y  L  R  Q  H  V  Q  Q  S  A  V  S  G  T  E  S  A  L

FIG. 14A

```
GAAGCGGATGAACTCGAGTTGCGCGGGTGCTCGCAGCTTGC          100
 E  A  D  E  L  E  L  R  R  V  L  A  A  C

TGCACCGGAGCCTACCCTGCCGAAGCTGGATATCGCTGCGG          200
 H  R  E  P  T  L  P  K  L  D  I  A  A  A

GCGGATGGTCGGTCGCCTGGCGGTCGCTGCCTCGGTGACCCT         300
 R  M  V  G  R  L  A  V  A  A  S  V  T  L
            △ CF1
CAACAGGGGACC[A]CCCCGCAGATCGCCCTGCCTCAG[TGA]AA      400
 Q  Q  G  T     P  Q  I  A  L  P  Q  V  K

ACTCCCTCGTCCAGCGATACCCGCTGGCATGAGCAGCGTCTGC        500
 S  S  S  D  T  R  W  H  E  Q  R  L  P

GCCCTACGCTCGGGCCAGCCTGGAAAACCGCTGA                 595
 P  Y  A  R  A  A  S  L  E  N  R  *
```

FIG. 14B

DETECTION OF CONVERSION TO MUCOIDY IN *PSEUDOMONAS AERUGINOSA* INFECTING CYSTIC FIBROSIS PATIENTS

Research leading to the present invention was supported in part by NIH grant AI 31139 The U.S. government therefore has certain rights in the invention.

BACKGROUND OF THE INVENTION

Cystic Fibrosis (CF) is the most common inheritable lethal disease among caucasians. There are approximately 25,000 CF patients in the U.S.A. The frequency of CF in several other countries (e.g., Canada, United Kingdom, Denmark) is high (ranging from 1 in 400 to 1 in 1,600 live births). There are numerous CF centers in the U.S.A. and Europe—specialized clinical facilities for diagnosing and treating children and adolescents with CF.

Chronic respiratory infections caused by mucoid *Pseudomonas aeruginosa* are the leading cause of high morbidity and mortality in CF. The initially colonizing *P. aeruginosa* strains are nonmucoid but in the CF lung they inevitably convert into the mucoid form. The mucoid coating composed of the exopolysaccharide alginate leads to the inability of patients to clear the infection, even under aggressive antibiotic therapies. The emergence of the mucoid form of *P. aeruginosa* is associated with further disease deterioration and poor prognosis.

The microcolony mode of growth of *P. aeruginosa*, embedded in exopolysaccharide biofilms in the lungs of CF patients (Costerton et al., 1983), among other functions, plays a role in hindering effective opsonization and phagocytosis of *P. aeruginosa* cells (Pier et al., 1987; Pier 1992). Although CF patients can produce opsonic antibodies against *P. aeruginosa* antigens, in most cases phagocytic cells cannot effectively interact with such opsonins (Pressler et al., 1992; Pier et al., 1990; Pier 1992). Physical hindrance caused by the exopolysaccharide alginate and a functionally important receptor-opsonin mismatch caused by chronic inflammation and proteolysis are contributing factors to these processes (Pedersen et al., 1990; Tosi et al., 1990; Pier, 1992). Under such circumstances, the ability of *P. aeruginosa* to produce alginate becomes a critical persistence factor in CF; consequently, selection for alginate overproducing (mucoid) strains predominates in the CF lung.

Synthesis of alginate and its regulation has been the object of numerous studies (Govan, 1988; Ohman et al., 1990; Deretic et al., 1991; May et al., 1991). It has been shown that several alginate biosynthetic genes form a cluster at 34 min of the chromosome (Darzins et al., 1985), and that the algD gene, encoding GDPmannose dehydrogenase, undergoes strong transcriptional activation in mucoid cells (Deretic et al., 1987; 1991). GDP mannose dehydrogenase catalyzes double oxidation of GDP mannose into its uronic acid, a reaction that channels sugar intermediates into alginate production. The transcriptional activation of algD has become a benchmark for measuring molecular events controlling mucoidy (Deretic et al., 1991; Ohman et al., 1990; May et al., 1991). Studies of these processes have lead to the uncovering of several cis- and trans-acting elements controlling algD promoter activity: (i) The algD promoter has been shown to consist of sequences unusually far upstream of the mRNA start site (Mohr et al., 1990). These sequences (termed RB1 and RB2), as well as a sequence closer to the mRNA start site (RB3) are needed for the full activation of algD (Mohr et al., 1990; 1991; 1992). (ii) AlgR, a response regulator from the superfamily of bacterial signal transduction systems (Deretic et al., 1989), binds to RB1, RB2, and RB3, and is absolutely required for high levels of algD transcription (Mohr et al., 1990; 1991; 1992). (iii) Another signal transduction factor, AlgB, also contributes to the expression of genes required for alginate synthesis (Wozniak and Ohman, 1991). (iv) The peculiar spatial organization of AlgR binding sites imposes steric requirements for the activation process. The conformation of the algD promoter appears to be affected by histone like proteins [e.g. Alg ($H_p1$) (Deretic et al., 1992) and possibly IHF (Mohr and Deretic, 1992)], and perhaps by other elements controlling nucleoid structure and DNA topology. (v) The algD promoter does not have a typical −35/−10 canonical sequence (Deretic et al., 1989). It has been proposed that RpoN may be the sigma factor transcribing this promoter; however, several independent studies have clearly ruled out its direct involvement (Mohr et al., 1990; Totten et al., 1990). The present inventors have cloned and characterized a new gene, algU, which plays a critical role in algD expression (Martin et al., 1993). The algU gene encodes a polypeptide product that shows sequence and domainal similarities to the alternative sigma factor Spo0H from Bacillus spp. (Dubnau et al., 1988). Spo0H, although dispensable for vegetative growth, is responsible for the initial events in the triggering of the major developmental processes in *Bacillus subtilis*, viz. sporulation and competence (Dubnau et al., 1988; Dubnau, 1991). These findings suggest that activation of alginate synthesis may represent a cell differentiation process participating in interconversions between planktonic organisms and biofilm embedded forms in natural environments (Martin et al., 1993; Costerton et al., 1987).

Inactivation of algU abrogates algD transcription and renders cells nonmucoid, further strengthening the notion that algU plays an essential role in the initiation of mRNA synthesis at algD (Martin et al., 1993). algU maps in the close vicinity of muc markers that have been demonstrated in the classical genetic studies by Fyfe and Govan (1980) to cause the emergence of mucoid strains constitutively overproducing alginate. The mucoidy-causing property of muc mutations has been based on the ability of different muc alleles (e.g. muc-2, muc-22, and muc-25) to confer mucoidy in genetic crosses (Fyfe and Govan, 1980; 1983). The present application describes the presence of additional genes immediately downstream of algU, termed mucA and mucB, which also play a role in the regulation of mucoidy.

Detection of mucoid *P. aeruginosa* is a standard practice, however, due to the variability in expression of mucoidy on standard clinical media, more objective detection methods are needed. An early detection of conversion to mucoidy will be possible by using the present invention.

SUMMARY OF THE INVENTION

The present invention provides compositions and methods for the early detection and diagnosis of the conversion to mucoidy of *Pseudomonas aeruginosa*.

The present invention also provides a molecular mechanism for the conversion from the nonmucoid to the mucoid state, including specific sequence alterations that occur in the mucA gene that cause the conversion and molecular probes for the early detection of this disease state.

The present invention provides a composition of matter comprising a first polynucleotide having the sequence of FIG. 9A, FIG. 9B, and FIG. 9C or FIG. 14, a second polynucleotide complementary to the first polynucleotide or a polynucleotide differing from the first or second polynucleotide by codon degeneracy. Also claimed is a polynucleotide which hybridizes with the first or second polynucleotide, or an oligonucleotide probe for the first or second polynucleotide which hybridizes with said polynucleotide.

A further composition of matter of the present invention is a *Pseudomonas aeruginosa* mucA or mucB gene in substantially pure form. The mucA gene is defined as substantially comprising the sequence of FIG. 14. Also claimed is a mucA gene defined further as having an altered sequence. The alteration may be an insertion or deletion of at least one nucleotide or it may be a frameshift mutation. In alteration of the gene results in an inactive mucA gene product. In a preferred embodiment of the invention, the altered gene sequence has a deletion of nucleotide "A" from position 371 of the sequence of FIG. 14.

The polynucleotide may be a polydeoxyribonucleotide or a polyribonucleotide. The oligonucleotide may be an oligodeoxyribonucleotide or an oligoribonucleotide. A further composition of matter is an oligonucleotide useful as a probe for and which hybridizes with the polynucleotide sequence of FIG. 14 or sequence alterations thereof. A preferred embodiment of the invention is an oligonucleotide comprising a sequence complementary to a region spanning the deletion at position 371. In particular, the oligonucleotide comprises the sequence 5'-GGGACCCCCCGCA-3'SEQ ID NO: 2. The altered sequence of the mucA gene may have a deletion of the nucleotide "G" from position 439 or 440. One skilled in the art would see that since there is a "G" in both positions 439 and 440 it is not possible to know which "G" is deleted in this altered sequence.

A further embodiment of the present invention is an oligonucleotide comprising a sequence complementary to a region spanning the deletion at position 439 or 440. In particular, this oligonucleotide comprises the sequence 5'-GAGCAGGGGCGCC-3'.

A further composition of matter of the present invention is a mucA gene having an altered sequence wherein the altered sequence is an insertion of nucleotides 5'-CAGGGGGC-3' between positions 433 and 434. Also claimed is an oligonucleotide comprising a sequence complementary to a region spanning the insertion of the nucleotides 5'-CAGGGGGC-3'. A preferred embodiment is an oligonucleotide comprising 5'-CAGGGGGC-CAGGGGGC-3'.

A further embodiment of the present invention is the use of these compositions of matter for a method of detecting conversion to mucoidy in *Pseudomonas aeruginosa* comprising detecting a loss of mucA or mucB function. In particular, a method of detecting conversion to mucoidy in *Pseudomonas aeruginosa* having an inactive mucA or mucB gene product comprising the detection of an altered sequence in the mucA or mucB gene is claimed. A preferred embodiment is a method of detecting conversion to mucoidy in *Pseudomonas aeruginosa* having an inactive mucA gene product comprising the detection of an altered sequence in the mucA gene. In this case, the altered sequence encodes an inactive product and the altered sequence is detected by hybridization with a complementary oligonucleotide. The complementary oligonucleotide may be 5'-GGGAC-CCCCCGCA-3'SEQ ID NO: 2, 5'-GAGCAGGGGCGCC-3', or 5'-CAGGGGGCCAGGGGGC-3'. One skilled in the art could see that an altered sequence may comprise nucleotide changes, insertions or deletions anywhere within this locus between about positions 300 and 500 of the sequence of FIG. 14.

A further embodiment of the present invention is a method of detecting conversion to mucoidy in *Pseudomonas aeruginosa* having an inactive mucA gene comprising the steps of: 1) obtaining *Pseudomonas aeruginosa* suspected of conversion to mucoidy to provide a test sample, and 2) hybridizing the test sample with an oligonucleotide 5'-GG-GACCCCCCGCA-3'SEQ ID NO: 2, 5'-GAG-CAGGGGCGCC-3', or 5'-CAGGGGGCCAGGGGGC-3'. Positive hybridization indicates conversion to mucoidy in *Pseudomonas aeruginosa*.

A further embodiment of the present invention is a *Pseudomonas aeruginosa* algU gene in substantially pure form. The algU gene comprises the sequence of FIG. 6.

ABBREVIATIONS

PAO1=nonmucoid strain of *P. aeruginosa*, mucA+
PAO568=mucoid strain of *P. aeruginosa* carrying the muc-2 mutation
TC'=tetracycline resistance
PAO578=mucoid derivative of PAO carrying the muc-22 mutation
oligO 568 (mucA2)=5'CAGGGGGCCAGGGGGC-3'
oligo 578 (mucA22)=5'-GAGCAGGGGCGCC-3'
oligo CFl=5'-GGGACCCCCCGCA-3'SEQ ID NO: 2

BRIEF DESCRIPTION OF THE DRAWINGS

FIG. 1A. Genetic map of the late region of the *P. aeruginosa* chromosome. Genetic markers pru-70, pruAB, hisI, and proB, are linked with the muc loci. muc-2, muc-22, and algU are cotransducible with pruAB (indicated by arcs). muc-25 and muc-3739 map between hisI and pur-70; it is not known whether they are cotransducible with pruAB (indicated by asterisks). The muc-23 marker maps between hisI and proB. FIG. 1B. Positions of several genetic markers, alg genes and probes used in this study on a physical map (SpeI) of *P. aeruginosa* PAO. The algD gene hybridizes to two SpeI fragments. Fragments E (360 kb), F (330 kb), and G (310 kb) are enlarged. The genetic map of the late region and the corresponding SpeI fragments are aligned to permit overlaps of markers known to hybridize to a given fragment, but precise relative positions are not known. Probes known to hybridize, or are shown here to hybridize, to a given SpeI fragment are displayed below corresponding fragments.

FIG. 2B. Position of the coding region for P27 (the algU gene), as determined by its expression in a T7 system. Overhead arrow, direction of algU transcription. P27 and P20, two polypeptides of 27.5 kDa and 20 kDa, respectively, detected in expression studies (see Results). Filled triangle, T7 promoter. +and –, production or no production, respectively, of corresponding polypeptides by a given construct.

FIG. 6. DNA sequence of algU. Bent arrows denote the endpoints of deletions: U4/76 suppresses mucoidy and produces P27 (+); U4/33 has no effect on mucoidy and is not capable of producing P27 (–). EcoRV, a site used for insertional inactivation of algU on the chromosome is shown. The nucleic acid sequence is SEQ ID NO:9 and the encoded amino acid sequence is SEQ ID NO:19.

FIG. 8. T7 expression analysis of mucB. Shown are $^{35}$S labeled polypeptides separated by SDS-polyacrylamide gel electrophoresis and visualized by autoradiography. Lanes: 1, pT 7–6 with a 3.1 kb clone of the deletion product U4/39 (FIG. 1A and FIG. 1B); 2, pT 7–6 with a 2.1 kb clone of the deletion product U4/33 (FIG. 1A and FIG. 1B); 3 and 4, same as 1 and 2, respectively, but inserts were cloned in pT 7–5. The mucB gene is in the direction of transcription from the T7 promoter in pT7–6 clones (lanes 1 and 2). In pT7–5 the clones are in the direction opposite to the T7 promoter. Only the region of the gel containing p33 is shown. Triangle denotes P33.

FIG. 9. The complete nucleotide sequence of mucA and mucB. The open reading frames compatible with the direction of transcription, suppression activity of deletions, and the observed $M_r$ of the mucA gene product [20 kDa (Martin et al., 1992)] and that of the mucB gene product (32.8 kDa; FIG. 2A and FIG. 2B) are shown. The end of the algU gene encoding a polypeptide homologous to sigma factor from Bacillus spp. (Martin et al., 1993) is shown. SD, putative ribosomal binding sites. Stars underneath the sequence, stop codons. The position of the BglII site used to insertionally inactivate mucB on the P. aeruginosa chromosome is shown. The end point of deletion UM9 that does not suppress mucoidy in PAO581 (muc-25) is shown (bent arrow). This deletion still partially suppresses mucoidy (indicated by asterisk; see FIG. 7 for definition) in PAO568 (muc-2). These sequence data have been submitted to GenBank (accession numbers L04794). The nucleic acid sequence is SEQ ID NO:10 and the encoded amino acid sequences are SEQ ID NOS:16–18, respectively.

FIG. 12A and FIG. 12B demonstrates allele-specific oligonucleotides for detection of muc mutations. Oligonucleotides used to detect muc mutations in mucoid PAO derivatives and CF isolates. FIG. 12A. The sequence of mucA from the position 425 to the position 455 given in FIG. 2A and FIG. 2B and oligonucleotides 568, 578, and 381 are shown. Highlighted nucleotide on the top line (and in oligonucleotides where it is present) indicates the base deleted in the mucA22 allele (also absent in the mucoid cystic fibrosis isolates CF14 and CF23). A stretch of highlighted nucleotides at the 5' end of the oligo 568 indicate 8 bp duplication of that sequence (causing frameshift equivalent to deletion of one nucleotide). The nucleic acid sequence is SEQ ID NO:10 and the encoded amino acid sequences are SEQ ID NOS:16–18, respectively. FIG. 12B. The sequence of mucA from positions 360 to 390 (see FIG. 2A and FIG. 2B) and oligonucleotides hybridizing to the wild type sequence (oligo 356/377) and to CF isolates that have a deletion within this region (bold letter) are shown. Dash, deletion of the corresponding nucleotide. The sequences are SEQ ID NOS:11, 4, 3, 12, 13, 2 and 14, respectively.

FIG. 14 shows the complete nucleotide sequence of the mucA gene from the standard genetic Pseudomonas aeruginosa strain PAO1 and specific nucleotide changes detected in different mucoid PAO derivatives and CF isolates. Highlighted nucleotides, single base pair deletions in cystic fibrosis isolates CF1, CF14, CF23, and in PAO578 (mucA22). Arrow above the sequence, insertion of 8 nucleotides in mucA2 strain PAO568 (for the sequence see FIG. 3A and FIG. 3B, oligo 568; for detection by hybridization see FIG. 4). These deletions and insertions create frameshift mutations and cause premature termination of translation (boxed are termination codons caused by detected frameshifts). In the case of mucA2 and mucA22 (as well as in CF strains with mucA22-like mutations) the same termination codon, overlapping with the BclI site is being used. The nucleic acid sequence is SEQ ID NO:1 and the encoded amino acid sequence is SEQ ID NO:15.

FIG. 17A. Under conditions when all genes are complete, MucA and MucB negatively regulate algU. One possibility shown here is that MucA and MucB are complexed with algU. This renders algU inactive or unavailable for transcription of algD (block). Despite all proteins being synthesized, including AlgR (a member of bacterial signal transduction systems, also required for algD transcription), due to the sequestering or inactivity of the sigma factor-like element algU (homologous to SigH, an alternative sigma factor controlling sporulation in Bacillus subtilis), there is no transcription of algD. FIG. 17B. When mucA is inactivated by a frameshift mutation, algU becomes active and allows initiation of transcription at algD. This results in mucoidy which in the CF lung affords protection against effective opsonization and phagocytosis, leading to chronic and intractable respiratory infections.

DETAILED DESCRIPTION OF THE PREFERRED EMBODIMENTS

Mucoidy in Pseudomonas aeruginosa is a critical virulence factor associated with chronic infections in cystic fibrosis (CF). The initially colonizing strains are nonmucoid but once in the CF lung, they almost inevitably convert into mucoid phenotype. Three tightly linked genes algU, mucA, and mucB have been identified with a chromosomal region shown by genetic means to represent the site where mutations cause conversion to mucoidy. Mutations causing mucoidy occur in mucA. The complete nucleotide sequence of the mucA gene is shown in FIG. 14. The positions of mutations in PAO568 (muc-2), PAO578 (muc-22), and CF isolates (CF1, CF14, and CF23) are also indicated in FIG. 14. The oligonucleotides designed to detect such mutations by hybridization are shown in FIG. 12.

Figure 17A:
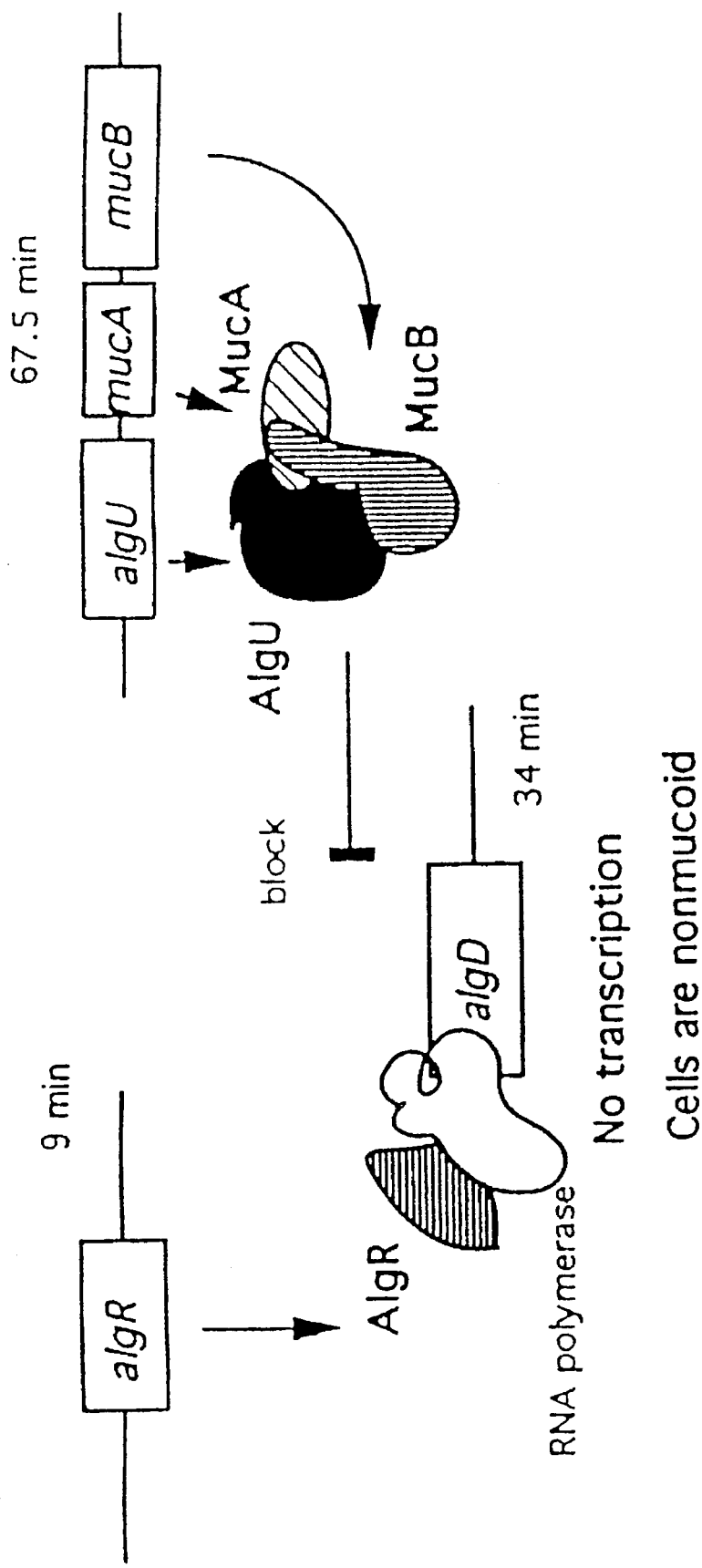
FIG. 17A and FIG. 17B shows regulatory circuits controlling mucoidy in P. aeruginosa and effects of muc mutations.
Figure 17B:
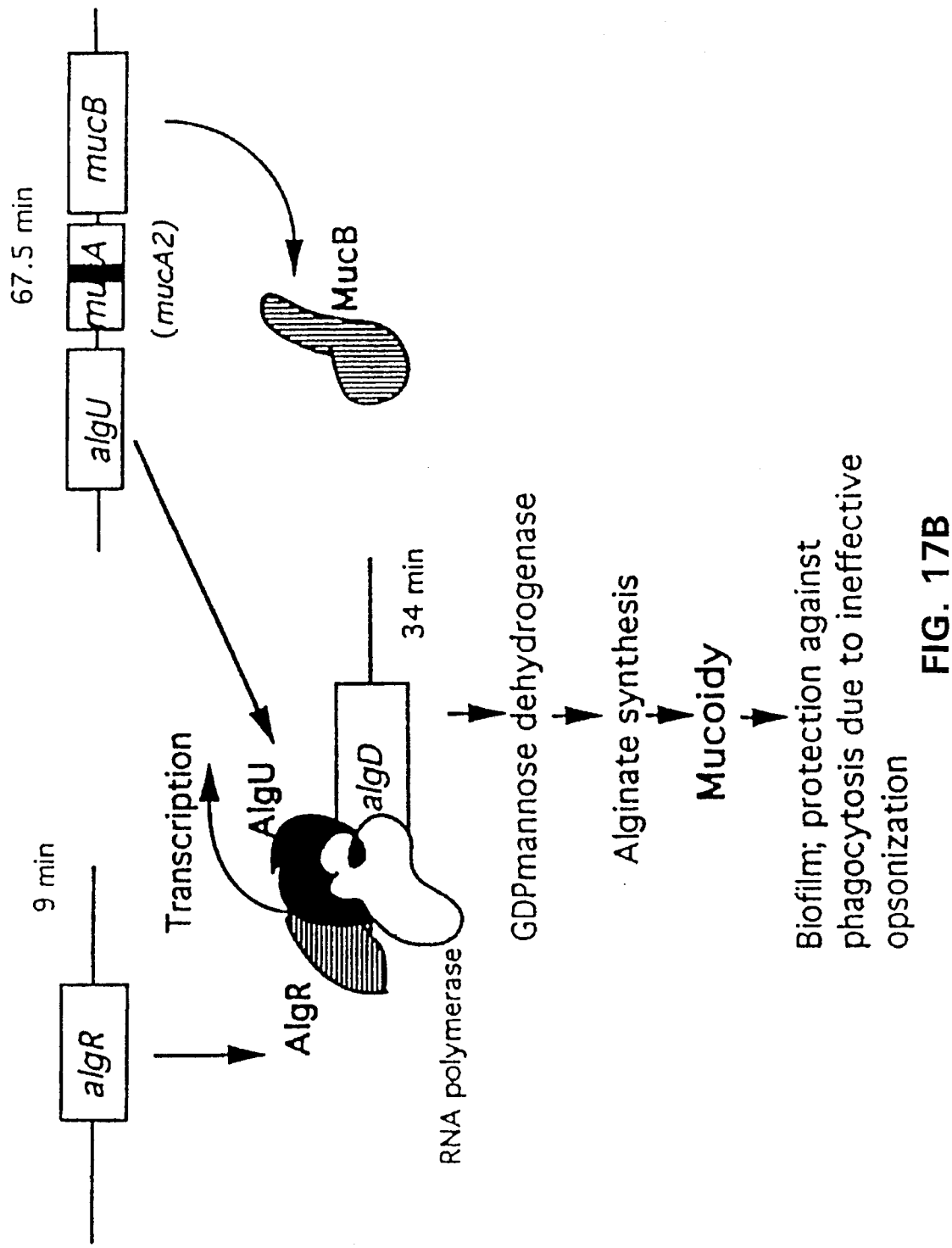

The algU gene plays a positive regulatory role in the transcription of algD, a gene encoding GDPmannose dehydrogenase. The algD gene must be expressed at high levels in order for cells to attain mucoid phenotype (FIG. 17A and FIG. 17B). mucA and mucB play a negative regulatory role, and, when active, these genes suppress mucoidy. When either mucA or mucB are inactivated, this results in derepression of algD transcription and conversion to mucoidy (FIG. 17A and 17B). The present inventors have isolated, sequenced, and characterized the entire region containing algU, mucA, and mucB. When a clone of algU, mucA and mucB, isolated from nonmucoid cells, is placed into mucoid derivatives of the standard genetic strain PAO and in CF isolates, it can cause suppression of mucoidy, viz. the cells become phenotypically nonmucoid and the algD promoter is silenced. Using gene replacements on the chromosome and phage-mediated generalized transduction, the present inventors have shown that algU and the downstream genes described here as mucA and mucB map at about 67.5 minutes on the P. aeruginosa chromosome. These genetic markers represent a site where mutations causing conversion from nonmucoid to mucoid phenotype occur, and have not been previously isolated or characterized. Mutations (deletions and insertions) causing frameshift mutations and premature termination of the mucA open reading frame have been identified through the work described herein (FIGS. 12A, 12B, and FIG. 14).

Even though the invention has been described with a certain degree of particularity, it is evident that many alternatives, modifications, and variations will be apparent to those skilled in the art in light of the foregoing disclosure. Accordingly, it is intended that all such alternatives, modifications, and variations which fall within the spirit and the scope of the invention be embraced by the defined claims.

The following examples are presented to describe preferred embodiments and utilities of the present invention, but should not be construed as limiting the claims thereof.

Example 1 describes the characterization of algU, example 2 describes the characteristic of mucB and example 3, mucA.

EXAMPLE 1

Characterization of a Locus Determining the
Mucoid Status of *Pseudomonas aeruginosa*: algU
Shows Sequence Similarities with a Sigma Factor
from Bacillus

MATERIALS AND METHODS

Media and bacterial growth. *E. coli* was grown on LB supplemented with 10 μg/ml tetracycline (Tc), 40 μg/ml ampicillin (Ap), and 25 μg/ml kanamycin (Km) when required. *P. aeruginosa* was grown on LB, minimal media (12,44), and Pseudomonas isolation agar (PIA) (DIFCO). The nitrogen free medium (P), used to test the ability to utilize proline (supplemented at the concentration of 20 mM) as the sole carbon and nitrogen source, has been previously described (44). Other amino acids were supplied as 1 mM when necessary. Media for environmental modulation by different nitrogen sources (nitrate or ammonia) have been described previously (12,50). 300 mM NaCl was added to LB when required (12). Antibiotics supplements for *P. aeruginosa* were: 300 μg/ml Tc for PIA, 50 μg/ml Tc for LB and minimal media, and 300 μg/ml carbenicillin (Cb) for all media.

Plasmids and bacterial strains. Strains of *P. aeruginosa* and plasmids used in this study are shown in Table 1.

TABLE 1

Bacterial strains, plasmids, and bacteriophages.

| Species, strain, plasmid, or phage | Relevant properties[a] | Reference |
|---|---|---|
| *P. aeruginosa* | | |
| PAO1 | prototroph Alg$^-$ | 31 |
| PAO1293 | prototroph Alg$^-$ | 55 |
| PAO568 | FP2$^+$muc-2 (Alg$^{+i}$) leu-38 | 24 |
| PAO578 | FP2$^+$ muc-22 (Alg$^+$) leu-38 | 24 |
| PAO579 | FP2$^+$ muc-23 (Alg$^+$) leu-38 | 24 |
| PAO581 | FP2$^+$ muc-25 (Alg$^+$) leu-38 | 24 |
| PAO540 | cys-5605 his-5075 argA171 Alg$^-$ | 24 |
| PAO669 | FP2$^+$muc-2 (Alg$^{+i}$) leu-38 Cb$^4$ algD$^+$ algD::xylE (Derived from PAO568) | This work |
| PAO670 | FP2$^+$ algU::Tc$^4$ (Alg$^-$) (Derived from PAO568) | This work |
| PAO964 | pru-354 ami-151 hut C107 Alg$^-$ | 44 |
| PAM425 | muc-3739 (Alg$^+$) lys-13 | 43 |
| Plasmids | | |
| pLA2917 | IncP1 mob$^+$ tra cos$^+$Tc$^r$ Km$^r$ | 1 |
| pCMob | ColE1 mob$^+$ (RK2) tra cos$^+$ Ap$^4$ (Cb$^4$) Tc$^r$ | 47 |
| pSF4 | Ori (p15A) mob$^+$ (RK2) cos$^+$ Tc$^r$ | 57 |
| pRK2013 | ColE1 mob$^+$ tra$^+$ (RK2) Km$^r$ | 21 |
| pT7-5 | ColE1 Ap$^r$φ10 promoter-EcoRI-polylinker- HindIII | 60 |
| pT7-6 | ColE1 Ap$^r$φ10 promoter-HindIII-polylinker-EcoRI | 60 |
| pGP1-2 | Ori (p15A) P$_L$T7 gene 1 (T7 RNA polymerase)P$_{lac}$-c1857 Km$^r$ | 60 |
| pVDZ'2 | IncP1 mob$^+$ tra lacZ' (lacZ_) Tc$^r$ | 9 |
| pCMR7 | algR as 827 bp HindIII-BamHI in pT7-6 | 48 |
| pPAOM3 | pVDX18 IngQ/P4 algD::xylE Ap$^r$ (Cb$^4$) | 37 |
| pMO011809 | hisI$^+$ (cosmid clone in pLA2917) | 55 |
| pMO012046 | algU$^+$ (cosmid clone in pLA2917) | This work |
| pDMU1 | algU$^+$ (a 6 kb HindIII-EcoRI fragment from pMO012046 subcloned on pVDZ'2) | This work |
| pDMU4/76 | algU$^+$ as Δ4/76 subcloned on pVDZ'2 | This work |
| pRCW1 | a 6 kb HindIII-NsiI subclone from the cosmid pMO011809 | This work |
| pDMU100 | pUC12 mob$^+$ algU::Tc$^r$ Ap$^r$ (Cb$^4$) | This work |
| pDMDX | pCMobB algD::xylE mob$^+$ Ap$^r$ (Cb$^4$) | |
| Phages | | |
| F116L | Generalized transduction phage | 40 |

[a]Alg$^{+i}$, inducible production of alginate resulting in mucoid phenotype (12). Alg$^+$, mucoid phenotype, Alg$^-$, nonmucoid phenotype.

Strains PAO669 and PAO670 were derivatives of *P. aeruginosa* PAO568 (muc- 2). The strain PAO669 was generated by integration of a nonreplicative plasmid carrying an algD::xylE fusion on the chromosome of PAO568. An 11.5 kb HindIII fragment carrying algD with xylE inserted in the XhoI site of algD, was cloned in the HindIII site of pCMobB (47), and the resulting plasmid pDMDX conjugated into PAO568. pCMobB and its derivative pDMDX cannot replicate in Pseudomonas but can be effectively mobilized into this bacterium (47). Cb$^r$ exconjugants were obtained and tested for the presence of other plasmid markers [development of a yellow color when sprayed with a solution of catechol (37)] and insertions on the chromosome verified by Southern blot analysis. The strain PAO669 was mucoid and produced alginate on inducing media. PAO670, a strain used to determine effects of the inactivation of algU on the chromosome, was constructed by gene replacement of the chromosomal algU with an insertionally inactivated algU (algU::Tc$^r$). This was accomplished as follows: A 2.4 kb HindIII-EcoRI fragment from Δ4/76 was inserted into pUC12. The resulting construct was digested with EcoRV, and NotI linkers were added. A NotI modified Tc$^r$ cassette (32) was inserted, and the resulting plasmid digested with EcoRI. Into this site an 1.4 kb EcoRI fragment with mob from pCMobA (originating from pSF4) (47,57) was inserted to produce pDMU100. This plasmid was transferred into *P. aeruginosa* PAO568 by conjugation and exconjugants selected on PIA supplemented with Tc. Since pUC12 and its derivative pDMU100 cannot replicate in Pseudomonas, Tc$^r$ strains had this plasmid integrated on the chromosome via homologous recombination. Double cross-over events were identified as Tc$^r$Cb$^s$ strains, chromosomal DNA extracted, digested with appropriate enzymes, and gene replacements verified by Southern blot analysis. CF strains were from a combined collection of mucoid isolates from CF patients in Edinburgh, Scotland, and San Antonio, Texas. Cosmid clones not shown in Table 1 are described in Results. The source of regA was a 1.9 kb PstI-XhoI subclone in mp18 (30). The use of *E. coli* strains for subcloning in pVDZ2 (JM83), triparental conjugations (HB101 harboring pRK2013), and deletion subcloning (WB373) has been described elsewhere (14,38).

Nucleic acids manipulations and recombinant DNA methods. All DNA manipulations and Southern blot analyses were according to the previously published methods (14,38, 50,55) or standard recombinant DNA procedures (3). Radiolabeled probes (3) were generated using random priming labeling method and [α-$^{32}$P]dCTP (3,000 Ci/mmol; DuPont NEN). RNA extraction and S1 nuclease analysis have been previously published (14,38). The construction of the cosmid clone library has been reported (55). Overlapping deletions of the clones in M13 were generated as previously described (14). DNA was sequenced by a modification of the chain termination method with the substitution of dGTP by its analog 7-deaza-dGTP to avoid compressions as previously described (38), and using 17 bp or custom made primers when needed. Similarity searches were performed using FASTA program (52) and GenBank databases, as well as through NBRF-PIR protein identification resource network server.

Genetic methods. clones made in broad host-range plasmids (pVDX18 and pVDZ'2) were transferred into *P. aeruginosa* by triparental filter matings as described previously (37), using *E. coli* harboring pRK2013 as the helper. Cosmid clones were mobilized into *P. aeruginosa* from *E. coli* S17–1 (58) as previously reported (55). Generalized transduction using F116L (40) was performed as follows: Serially diluted (to achieve near confluency) single plaque preparations of F116L were grown mixed with the donor strain in top agar for 17 h at 37° C. The top agar was scraped and phage eluted in equal volume of TNM (10 mM Tris-HCl pH 7.4, 150 mM NaCl, 10 mM MgSO$_4$), centrifuged at 9000 rpm in SM24 rotor, and supernatant filtered through a 0.45 μm membrane to generate transducing phage stock (used within one month). 500 μl of freshly grown overnight recipient cells was incubated with 500 μl of transducing phage stock (diluted to 5×10$^9$; multiplicity of infection 5:1) for 20 min at 37° C. Cells were centrifuged for 1 min in a microcentrifuge and resuspended in 1 ml of TNM. Aliquots were plated on selective media and incubated for 1 to 2 days, strains purified on selective media, and then spot tested for coinheritance of unselected markers.

Enzyme and alginate assays and scoring of suppression of mucoidy. Catechol 2,3-dioxygenase (CDO), the gene product of xylE, was assayed in cell-free sonic extracts as previously described (37). The activity was monitored in 50 mM phosphate buffer (pH 7.5)-0.33 mM catechol by following the increase of $A_{375}$ in a Shimadzu UV160 spectrophotometer. The molar extinction coefficient of the reaction product, 2-hydroxymuconic semialdehyde, is 4.4×10$^4$ at 375 nm. Suppression of mucoidy by plasmid borne genes was monitored on PIA plates unless specified otherwise, and the phenotypic appearance of the colonies scored as mucoid or nonmucoid. A control strain harboring the vector without an insert was always used for comparison. Alginate was assayed by a colorimetric method (36).

Visualization of gene products using T7 RNA polymerase/promoter system. Polypeptides encoded by cloned genes were visualized by expression in *E. coli* using a temperature-inducible T7 expression system (plasmid vectors pT7–5 and pT7–6 and T7 RNA polymerase encoded by pGP1–2) (60) and protein labeling with [$^{35}$S]methionine and [$^{35}$S]cysteine (Expre$^{35}$S$^{35}$S protein labeling mix; 1000 Ci/mmol; DuPont NEN) with previously described modifications (38,47). Proteins were separated on 12% sodium dodecyl sulfate-polyacrylamide gels. $^{14}$C-labeled methylated proteins (Amersham) were used as molecular weight standards. The gels were fixed in 10% acetic acid, washed with H$_2$O, impregnated with 1M salicylic acid, and bands representing radiolabeled polypeptides detected by autofluorography at −70° C.

Pulsed-field gel electrophoresis and Southern blot analysis. Localization of genes on the SpeI map of *P. aeruginosa* PAO was performed by previously published methods (55,59). Identification of SpeI fragments was done by comparison to the lambda phage concatameric ladder ranging in size from 48.5 to 582 kb (55) as well as based on the hybridization to the previously mapped genes (55,59).

Nucleotide Sequence accession number. The sequence reported here has been deposited in GenBank (accession number LO2119).

RESULTS

Figure 1A:
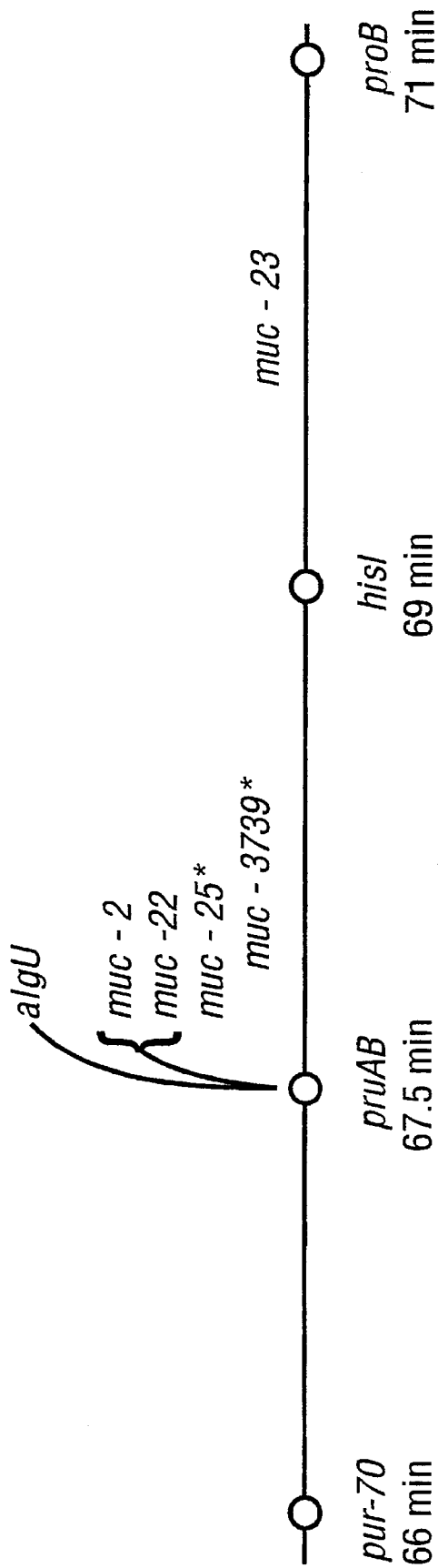
FIG. 1A and FIG. 1B. Location of muc loci and algU on genetic and physical maps of *P. aeruginosa* PAO.
Figure 1B:
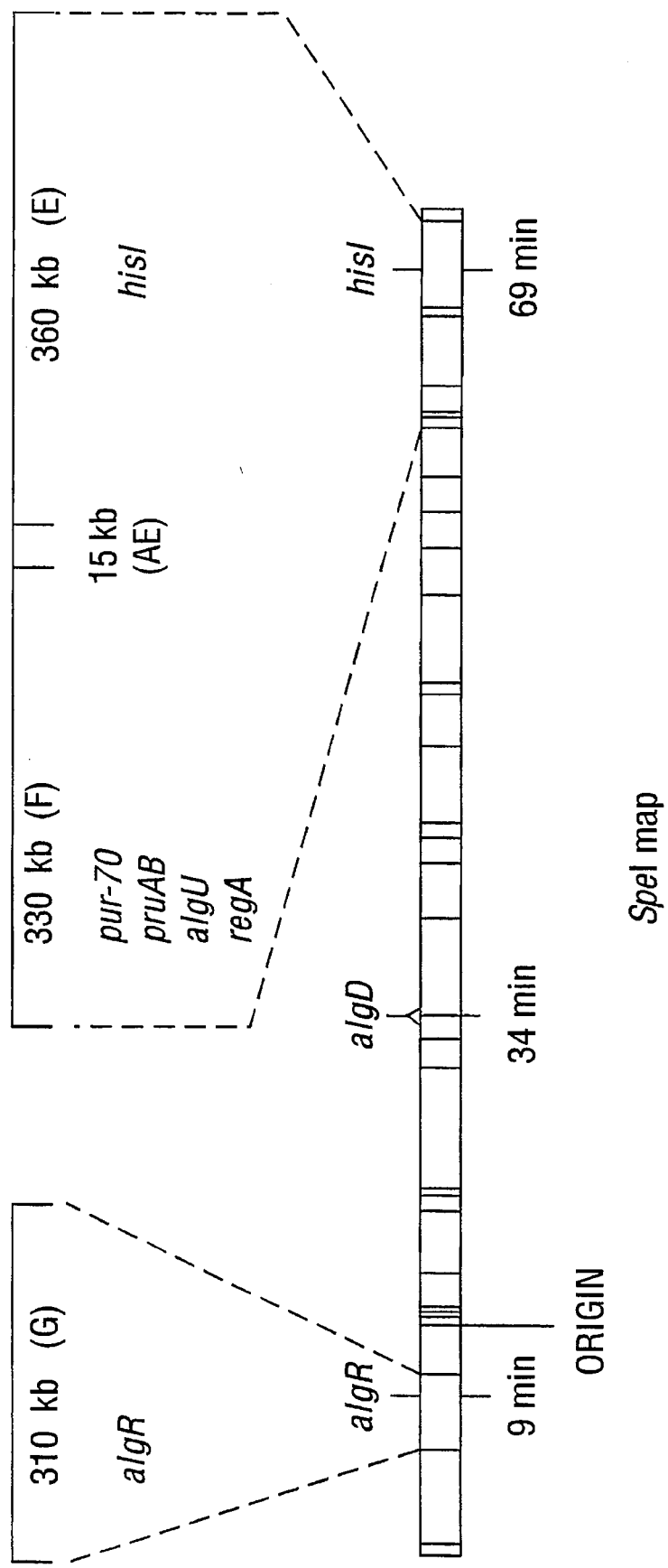

Isolation of cosmid clones affecting mucoidy in trans. Several genetic studies have indicated that muc loci have the property to affect mucoidy when present in trans. For example, it has been observed that R' derivatives of R68.45, which carry pruAB$^+$ and an adjacent muc locus from a nonmucoid PAO strain, are capable of switching off (suppressing) alginate production in mucoid strains PAO568, PAO578, and PAO581 (23). This effect appeared to be specific since another mucoid PAO derivative, strain PAO579, was not affected (23). This suggested to the present inventors that changes in mucoidy could be used as a screening tool to clone and isolate additional regulatory genes. A generation of a comprehensive genomic library from *P. aeruginosa* has been reported previously (55). Several cosmids from this library have been successfully used for construction of a combined physical and genetic map of *P. aeruginosa* PAO (55). This cosmid library was constructed in pLA2917 (which can replicate in *P. aeruginosa*) using DNA from a derivative of the strain PAO1 (nonmucoid) (31,55). The library was introduced into several mucoid strains by conjugation and ten independent and nonoverlapping clones capable of altering the mucoid character were isolated: pMO010533, pMO010921, pMO011021, pMO011537, pMO011644, pMO011744, pMO011801, pMO011809, pMO011920, and pMO012046. Two of the clones had previously been described as carrying other genetic markers (55). pMO011809 contains hisI and has been used to demonstrate that this locus resides on the SpeI fragment E (FIG. 1A and FIG. 1B, 360 kb) in the late region of the chromosome (55). In the same study, pMO011644 was shown to carry the oruI gene, also mapping in the late region of the chromosome, but hybridizing to a different SpeI fragment (FIG. 1A and FIG. 1B, 330 kb; fragment F). One of the clones, pMO012046, rendered a significant number of strains completely nonmucoid, and was chosen for further study. The locus affecting alginate production on this chromosomal fragment was designated algU.

Figure 2A:
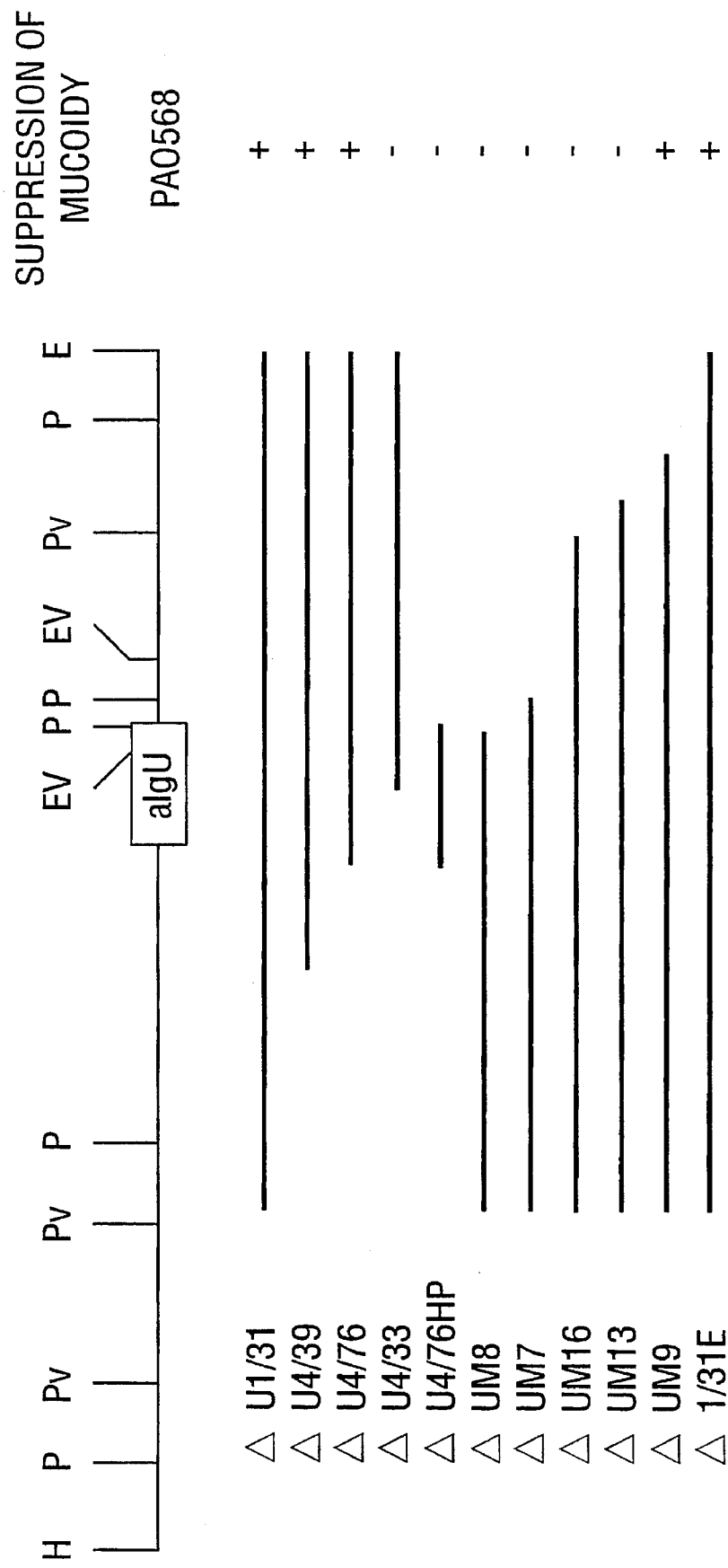
FIG. 2A and FIG. 2B. Deletion mapping of the algU locus. Different deletion products of a 6 kb HindIII-EcoRI fragment from pMO012046 which suppresses mucoidy in trans, were subcloned on the broad host range plasmid pVDZ'2, conjugated into PAO568 (muc-2), and exconjugants scored for the loss of mucoid phenotype. +, loss of mucoidy; no effect (mucoid phenotype retained). Lines represent regions spanned by DNA fragments. Only the location of algU is shown; the boundaries of other gene(s) (see text) are not known. Bar, 1 kb. Restriction sites: E, EcoRI; EV, EcoRV; H, HindIII; P, PstI; Pv, PvuII.
Figure 2B:
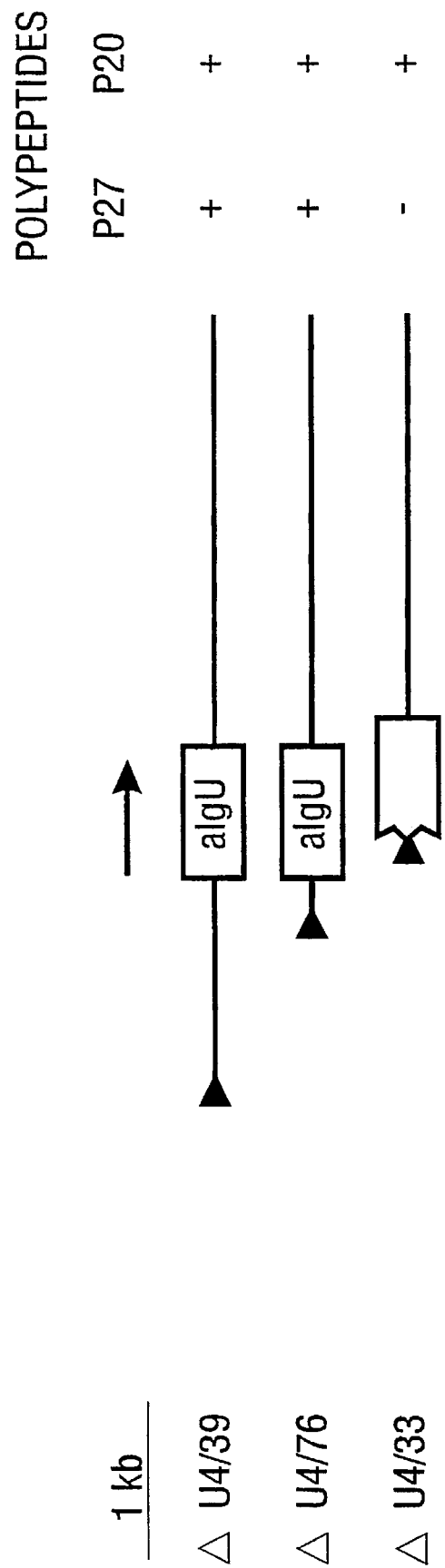

Deletion mapping of the algU locus. In order to facilitate molecular characterization of algU, this locus was examined by deletion mapping. The subcloning of the ability of algU to suppress alginate production and mucoid phenotype was done using the broad host range subcloning vector pVDZ'2 (9). Initially, a 6 kb HindIII-EcoRI fragment from pMO012046 was found to carry the suppressing activity, and was subjected to further deletion mapping. Two series of consecutive overlapping deletions were produced from each end of the 6 kb fragment (FIG. 2A and FIG. 2B), using the previously described deletion-subcloning strategy (14). Subclones of these deletion products in pVDZ'2 were transferred by conjugation into PAO568, a mucoid derivative of the standard genetic strain PAO (24). The exconjugants were screened for the loss of mucoid character. A summary of this analysis is shown in FIG. 2A. All deletion clones which retained the suppressing activity caused phenotypically indistinguishable effect; all negative deletions completely lost the ability to affect mucoidy. The activity was delimited to a region demarcated by the endpoints of deletions ΔU4/76 and ΔUM9.

algU has a strain-specific effect on suppression of mucoidy. It has been shown that different mucoid PAO derivatives and clinical CF isolates display significant differences in algD promoter activity and alginate production in response to modulation by environmental stimuli, such as the salt concentration in the medium or growth on nitrate (12). For example, the algD promoter in strains PAO568 and PAO578 is induced by salt or growth on nitrate (12), although the effects differ in magnitude. PAO568 and PAO578 carry muc determinants designated muc-2 and muc-22 (24), respectively, which map close to each other and to pruAB (23,25). PAO579 has a different muc locus (designated muc-23) which maps between hisI and proB (FIG. 1A and FIG. 1B) and displays a completely opposite response to increased salt concentration in the medium when compared to PAO568 and PAO578 (12). Another possibly different muc locus is represented by muc-3739 (strain PAM425) (43). When the plasmid pDMU1, containing an active algU locus on the 6 kb HindIII-EcoRI insert in pVDZ'2 was introduced into a panel of strains representative of different mucoid PAO derivatives and CF clinical isolates, a specific pattern of suppression of mucoidy was observed (Table 2).

TABLE 2

Strain specific suppression of mucoidy by algU.

| Strain[a] | pVDZ'2 | pDMU1 | Plasmid[b] pRCW1 Suppression of mucoidy[c] |
|---|---|---|---|
| PAO568 (muc-2) | − | + | − |
| PAO578 (muc-22) | − | + | − |
| PAO581 (muc-25) | − | + | − |
| PAO579 (muc-23) | − | − | − |
| PAM425 (muc-3739) | − | − | + |
| CF strains | − (18/18)[d] | + (7/18)[e] | + (3/8)[f] |

[a]PAO strains are isogenic mucoid derivatives of *P. aeruginosa* PAO381 carrying different mapped muc markers (24) (FIG. 1A and FIG. 2). PAM425 is a cross between PAO and a mucoid clinical *P. aeruginosa* isolate, Ps3739 (43); the corresponding muc-3739 locus has been mapped (43) (FIG. 1A and FIG. 1B). CF strains were mucoid *P. aeruginosa* isolates from different cystic fibrosis patients.
[b]pDMU1 is algU from PAO1 cloned as a 6 kb HindIII-EcoRI fragment on the broad host range vector pVDZ'2 (9). pRCW1 is a subclone of a 6 kb HindIII-NsiI fragment (see Results) from pMO011809 in pVDZ'2.
[c]Suppression was scored on PIA supplemented with Tc as + (transition from mucoid to nonmucoid status when harboring the plasmid) or − (the strain remained mucoid when harboring the plasmid).
[d]Of 18 strains tested none were affected by the vector pVDZ'2.
[e,f]Of 18 strains tested (denominator), 7 lost mucoidy when harboring pDMU1; of 8 strains (denominator) in which pRCW1 was introduced, 3 lost mucoidy. The strains affected by pDMU1 were different from those affected by pRCW1, except in one case with variable results. Not all strains tested with pRCW1 were tested with pDMU1 and vice versa.

pDMU1 rendered muc-2, muc-22 and muc-25 strains (PAO568, PAO578, and PAO581) nonmucoid. In contrast, it had no detectable effect on the muc-23 strain PAO579 and a muc-3739 strain (PAM425). It also affected a substantial number of mucoid clinical isolates (7 out of 18 tested). Congruent with these results was the finding that the mucoid phenotype of some of the strains not affected by algU were affected by a different clone. For example, the strain PAM425 which was not affected by pDMU1 lost its mucoid character when pRCW1, containing a 6 kb HindIII-NsiI subclone from the cosmid pMO011809 (55), was introduced (Table 2). pRCW1 affected 3 out of 8 CF isolates tested. Thus, the CF strains fell into three categories: (i) Those affected by pDMU1, (ii) those affected by pRCW1, and (iii) those not affected by either of the plasmids.

The results presented in this section indicated that: (i) The suppression of mucoidy in trans was strain dependent; (ii) algU affected a significant number of CF isolates; and (iii) there was a correlation between different muc linkage groups and different clones exerting effects.

Figure 3A:
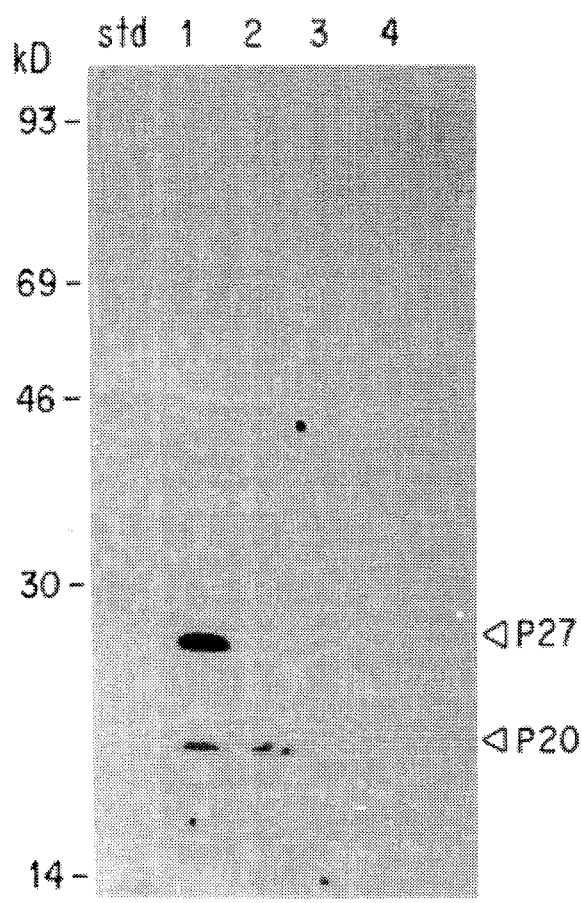
FIG. 3A and FIG. 3B. T7 expression analysis of polypeptides encoded by the algU locus. [$^{35}$S] methionine and [$^{35}$S] cysteine labeled polypeptides encoded by different deletion derivatives of the algU region were separated by SDS-polyacrylamide gel electrophoresis and visualized by autofluorography. Lanes and DNA constructs: std, [$^{14}$C]-labeled methylated protein standard (Amersham); 1, U4/39 cloned in pT7–6; 2, U4/33 cloned in pT7–6; 3, U4/39 cloned in pT7–5; 4, U4/33 cloned in pT7–5. Filled triangle, P27; stippled triangle, P20. Triangle at the beginning or end of a line designates the direction of transcription from the T7 promoter. Filled rectangle, the location of the gene encoding P27. The position of the gene encoding P20 (stippled rectangle) is shown arbitrarily. Ability of the insert to suppress mucoid phenotype in PAO568 (transition from mucoidy to nonmucoidy) when cloned in pVDZ'2 is indicated by a+ sign. –, no suppression of mucoidy.
Figure 3B:
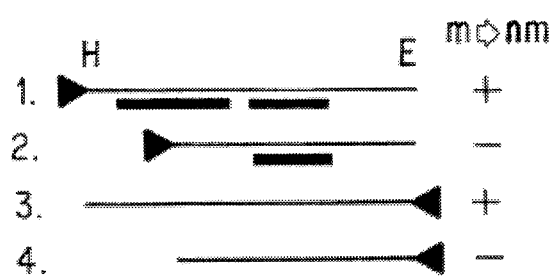

Two polypeptides, P27 and P20, are encoded by the region affecting mucoidy in muc-2, muc-22, and muc-25 strains. Since deletion inactivation of the algU locus from either end had similar effects, suppression of mucoidy was unlikely to be due to the titration of a diffusable factor (e.g. AlgR) by its binding to DNA. Whether this locus had a coding capacity for a possible trans-acting factor was tested by analysis of [$^{35}$S] methionine and [$^{35}$S] cysteine labeled polypeptides encoded by the insert in a T7 expression system. The results of these studies are illustrated in FIG. 3A and FIG. 3B. Two polypeptides, with apparent $M_r$ of 27.5 kDa (P27) and 20 kDa (P20) were observed as encoded by the algU containing DNA fragment. The consecutive deletions were then used to establish the order of genes and their importance for the suppressing activity (FIG. 3A and FIG. 3B). Deletions extending from the HindIII end abolished P27 synthesis while not affecting P20, thus establishing the order of genes as P27 followed by P20. The gene encoding P27 was designated algU. Deletion ΔU4/33, which lost the ability to produce P27, but still directed the synthesis of P20, was no longer capable of suppressing mucoidy. Thus, algU was necessary for the activity of this region.

Suppression of mucoidy by algU is exerted at the level of algD transcription. Both algD and algR undergo transcriptional activation in mucoid cells (14). The difference in transcription is very profound at the algD promoter, which remains silent in nonmucoid cells and is highly active in mucoid strains (11,12,14). algR is transcribed from two promoters, one distal and constitutive (47,50), and the other proximal and induced in mucoid cells (14). We investigated whether the presence of algU affected transcription of algD and algR. To assay algD transcription under different conditions in the presence of algU on a plasmid, we first constructed a transcriptional fusion of algD and xylE [used as a reporter gene (37)] on the chromosome of PAO568. The strain was constructed as a merodiploid for algD, with one intact copy of algD while the other was inactivated due to the fusion with xylE (strain PAO669; for construction details see Materials and Methods).

The parental strain PAO568 (24) has a remarkable feature in that it displays a broad dynamic range of algD expression (12). Both algD transcription and colony morphology (changing from nonmucoid to mucoid) respond dramatically to inducing conditions (high salt concentration in the medium or growth on nitrate) (12). The strain PAO669 retained these properties (since PAO669 was merodiploid for algD it could synthesize alginate). The induction of algD on the chromosome of PAO669 was analyzed to verify the previously established parameters of algD response to environmental conditions (12,37,50). The results of xylE fusion assays and phenotypic induction of mucoidy indicated that the chromosomal fusion reacted to environmental modulation in the same manner previously reported for algD-xylE fusions on plasmids (Table 3).

TABLE 3

Effects of plasmid borne algU from PAO1 on algD transcription in the muc-2 background.

| Strain and plasmids[a] | Phenotype[b] | LB | LB + NaCl | NH$_4$ | NO$_3$ |
|---|---|---|---|---|---|
| | | | CDO (U/mg)[d] | | |
| PAO669 [None] | M | 0.43 (ND) | 2.84 (ND) | 0.22 (±0.02) | 5.69 (±1.19) |
| PAO669 [pVDZ'2] | M | 0.76 (±0.14) | 4.61 (±1.19) | 0.59 (±0.10) | 3.25 (±0.47) |
| PAO669 [pDMU4/76] | NM | 0.39 (±0.08) | 0.40 (±0.08) | 0.20 (±0.03) | 0.20 (±0.02) |

[a]PAO669 is a derivative of PAO568 (muc-2) in which an algD-xylE fusion has been placed on the chromosome. The plasmid pDMU4/76 was constructed by cloning the deletion product U4/76 (FIG. 2A and 2B) into pVDZ'2. This plasmid suppresses mucoidy in muc-2, muc-22, and muc-25 PAO derivatives.
[b]Phenotype was scored on inducing media (PIA, LB + NaCl and NO$_3$). M, mucoid; NM, nonmucoid.
[c]Growth conditions and media were as previously reported (12). LB + NaCl, LB supplemented with 300 mM NaCl. NH$_4$ and NO$_3$, minimal media with ammonia or nitrate as the nitrogen source, respectively. The composition and the use of these media for algD induction have been previously described (12,50).
[d]Activity of catechol 2,3 dioxygenase (CDO), the xylE gene product, was determined in cell free extracts as previously described (37). One unit of CDO is defined as the amount of enzyme that oxidizes 1 μmol of catechol per min at 24° C. ±, standard error; ND, not determined.

When plasmid pDMU4/76, carrying algU and capable of suppressing mucoidy, was introduced into PAO669, this resulted in a complete loss of alginate synthesis and algD transcription. No induction was observed in response to environmental stimuli known to induce algD in PAO568 (12) (Table 3). When PAO669 harboring pDMU4/76, which displayed nonmucoid colony morphology, was transferred to a medium that no longer supplied selective pressure for plasmid maintenance, colonies segregated into outgrowing mucoid and nonmucoid sectors (data not shown). This was accompanied by a loss of the plasmid in mucoid segregants, as evidenced by the loss of Tc$^r$ in such cells. The Tc$^s$ bacteria (devoid of pDMU4/76) had algD activity restored, as indicated by activities of the chromosomal algD- xylE fusion in strains purified from the corresponding sectors. The mucoid segregants grown on PIA showed CDO (the xylE gene product) activities ranging from 1.76–2.01 U/mg, while the nonmucoid strains originating from the same colonies had CDO activities ranging from 0,401–0.445 U/mg of protein in crude cell extracts. The effects of algU on algD was confirmed by S1 nuclease protection analysis of algD mRNA levels (data not shown). The S1 nuclease protection experiments also indicated that neither of the algR promoters were affected in PAO568 harboring algU on a plasmid (not shown). These results strongly suggested that the effect of algU on mucoidy was at the level of algD transcription.

Figure 4A:
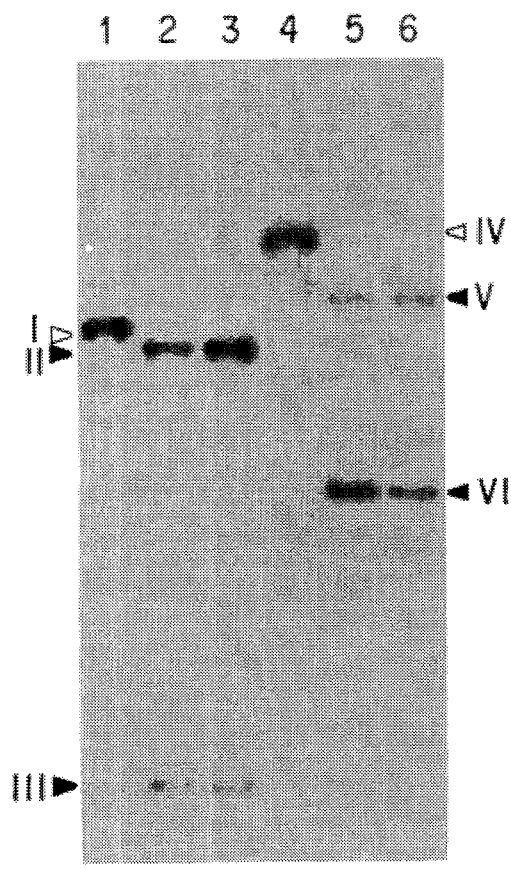
FIG. 4A and FIG. 4B. Insertional inactivation of algU on the PAO568 chromosome. Top panel, Southern blot analysis of chromosomal DNA from PAO568 (lanes 1 and 4) and from PAO670 (lanes 2 and 5) digested with HindIII-EcoRI (lanes 1,2) and NotI (lanes 4 and 5). Lanes 3 and 5 show HindIII-EcoRI and NotI digests, respectively, of another nonmucoid derivative of PAO568 which, like PAO670, underwent a gene replacement of algU with algU::Tc$^r$. The scheme below the blot shows events leading to the gene replacement in PAO670. The plasmid pDMU100 (oval) was constructed as described in Materials and Methods, conjugated into PAO568, and double cross-over mutants selected. Different algU variants and resulting restriction fragments in PAO568 and PAO670 are shown. I (HindIII-EcoRI) and II (NotI), chromosomal fragments of PAO568 hybridizing (open triangles) to the algU probe (U4/76). Filled triangles, fragments in PAO670 hybridizing with the probe: II and III, fragments detected after digestion with HindIII and EcoRI; V and VI, fragments detected after digestion with NotI. Oval, plasmid pDMU100 (thin line, vector sequences; thick line, algU insert). Filled rectangle, algU. Jagged edge indicates incomplete algU. Stippled rectangle, Tc$^r$ cassette. X, crossover points (chosen arbitrarily). Thick horizontal lines, chromosomal regions of PAO568 and PAO670, respectively. Thin lines, location of restriction fragments detected on the blot. // indicates that the fragment is longer than actually shown. Horizontal bar, 1 kb. Small vertical bars, restriction sites. N, NotI; N(EV), EcoRV site converted into NotI. Other sites as in FIG. 2A and FIG. 2B.
Figure 4B:
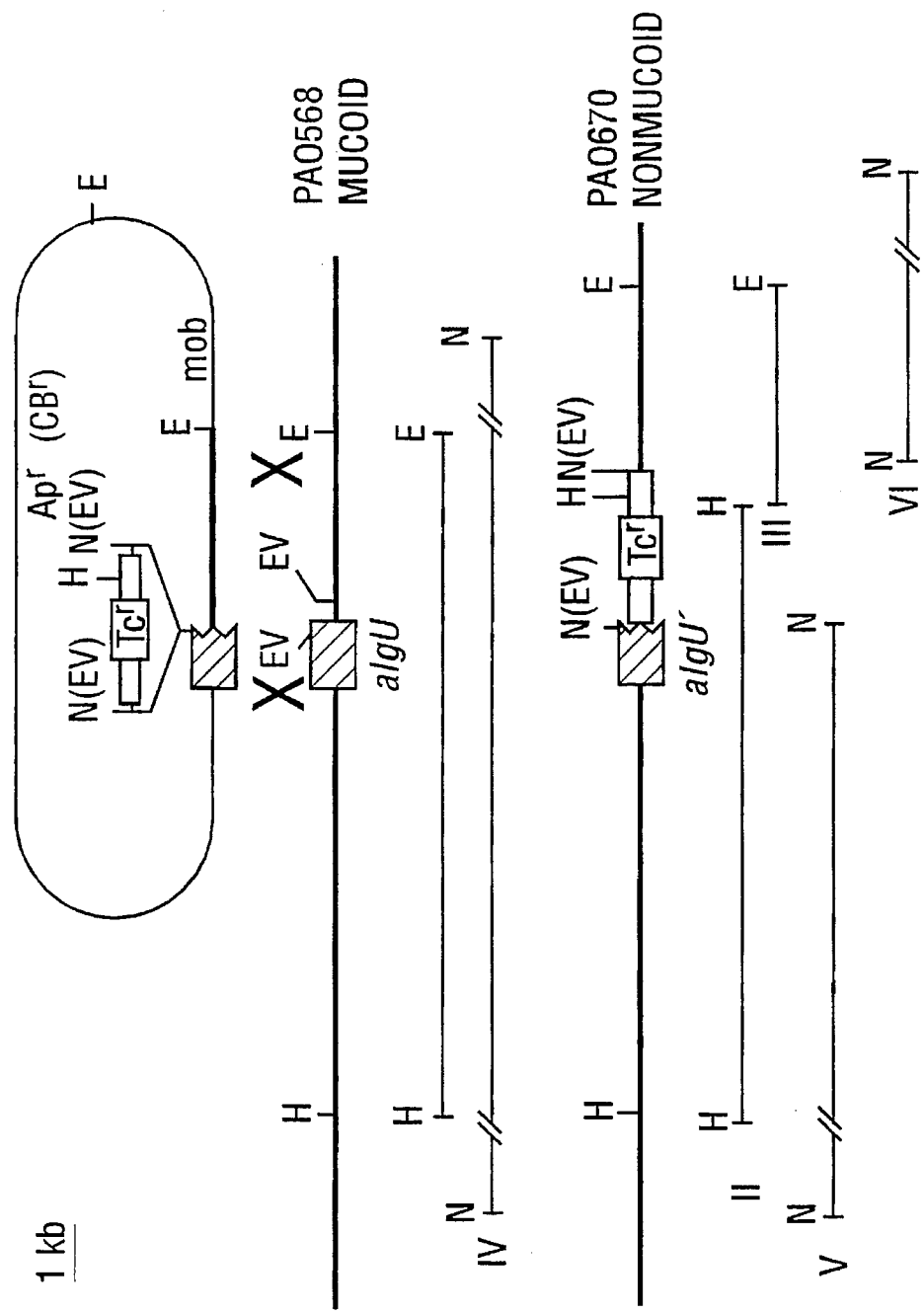

Insertional inactivation of the algU locus on the chromosome of PAO568 renders cells nonmucoid and abrogates algD transcription. The experiments presented in the previous sections were not sufficient to conclude that algU participates in algD promoter regulation under normal circumstances. In order to investigate this possibility, and to explore whether algU is a positive or a negative regulator of algD transcription, we insertionally inactivated this locus on the chromosome. Transposon mutagenesis of algU on a plasmid using Tn5 proved to be uninterpretable, possibly due to the reported instability of Tn5 in Pseudomonas (26) and was not pursued further. Instead, a Tc$^r$ cassette was inserted into a conveniently located restriction site within the algU region. These experiments were performed as follows: (i) The presence of two closely spaced EcoRV sites (FIG. 2A and FIG. 2B) was noted in the region where the gene encoding P27 (algU) resided. This was based on the estimated size of the gene needed to encode a 27.5 kDa polypeptide, the detailed mapping of the coding region of algU using T7 expression studies (summarized in FIG. 2B), and was further confirmed by DNA sequence analysis (see later sections). Since the endpoint of the last positive deletion still producing P27 was located 540 bp upstream from the first EcoRV site, we concluded that this site must be within the algU coding region. (ii) A suicide plasmid (pDMU100) was constructed (see Materials and Methods) in which the 2.4 kb HindIII-EcoRI fragment from ΔU4/76 was placed on pUC12 which cannot replicate in P. aeruginosa. EcoRV sites within the algU insert were converted into NotI specificity, and a Tc$^r$ cassette (32), modified as a NotI fragment, was inserted. After addition of a DNA fragment with the mob functions to facilitate plasmid mobilization into Pseudomonas (57), the final construct (pDMU100) was conjugated into PAO568 and Tc$^r$ exconjugants were selected. These strains were expected to have the plasmid with algU::Tc$^r$ integrated on the chromosome via homologous recombination. Two possible types of recombinants were anticipated: (i) Merodiploids for algU, retaining an active algU copy, which would have an insertion of the entire plasmid as the result of a single cross-over event; and (ii) true gene replacements, products of double cross-overs, in which case the plasmid moiety and the associated markers would be lost. We have observed in other gene replacement studies using this procedure that double cross-over events on the P. aeruginosa chromosome are frequent and that they range from 10% to 70% for various genes studied (unpublished results), obviating in all cases examined the need for a positive selection against markers encoded by the plasmid moiety. In 9 independent experiments with algU::Tc$^r$, 1663 Tc$^r$ exconjugants were examined. Of these 29% lost Cb$^r$ encoded by the plasmid moiety, indicative of double cross-over events. All such Tc$^r$Cb$^s$ strains were nonmucoid and did not produce alginate under any of the conditions tested. Most of the colonies with Tc$^r$ and Cb$^r$ markers (results of single cross-over events and thus expected to have a functional copy of algU) were mucoid, while a portion of such strains showed a delayed mucoid phenotype (mucoidy was developing after 3–4 days as compared with 48 hours needed for the parental strain PAO568). Further experiments with $Tc^rCb^s$ recombinants using Southern blotting analysis confirmed that these nonmucoid strains had a true gene replacement with the chromosomal copy of algU disrupted by the $Tc^r$ cassette (FIG. 4A and FIG. 4B). Moreover, when the mutation in such strains was purified by transduction (using the generalized transducing phage F116L) into the parental strain PAO568, all $Tc^r$ transductants displayed nonmucoid phenotype. One of the algU::$Tc^r$ derivatives characterized in these experiments (strain PAO670) was used to investigate algD transcription. This time, the previously characterized algD-xylE fusion plasmid pPAOM3 (37) was introduced into PAO670, and algD promoter activity assayed.

TABLE 4

Analysis of algD transcription in PAO670 (algU::$Tc^r$).

| Strain and plasmid[a] | Growth conditions[b] | | |
|---|---|---|---|
| | PIA | LB + NaCl | $NO_3$ |
| | | CDO (U/mg)[c] | |
| PAO568 [pPAOM3] | 12.10 | 11.54 | 10.95 |
| PAO670 [pPAOM3] | 1.02 | 1.85 | 1.40 |

[a]PAO568 (muc-2) is the mucoid parental strain of PAO670. PAO670 has algU insertionally inactivated on the chromsome. Both strains harbored the algD-xylE transcriptional fusion plasmid pPAOM3.
[b]PIA is a rich medium on which all mucoid strains, including PAO568, present their mucoid phenotype. Other media induce mucoidy and algD transcription in PAO568 (12) and are defined in Table 3.
[c]CDO, catechol 2,3 dioxygenase. Relative error did not exceed 20%.

These results (Table 4) indicated that inactivation of the algU locus on the chromosome resulted in a loss of algD transcription, and strongly suggested a positive role for algU in algD expression.

Genetic and physical mapping of algU indicates its close linkage or identity with a subset of muc loci. Plasmid borne algU showed specific suppression of mucoidy in strains containing muc- 2 and muc-22. These and other muc loci have been suggested to participate in the emergence of mucoid strains (24,43), although their nature and the mechanism of action have not been studied. Extensive information is available on the linkage of muc to genetic markers within the late region of the PAO chromosome (23,24,25,43) (FIG. 1A and FIG. 1B). Of particular significance is the cotransducibility of muc-2 and muc-22 with the pru-354 marker [a mutation in pruAB, genes required for the utilization of proline as the sole carbon and nitrogen source (44)] demonstrated by F116L bacteriophage mediated genetic exchange (23,25). This indicates that these muc loci and the pruAB genes are very close, since F116L can transduce regions in the range of one min of the chromosome.

The present inventors proceeded to localize algU on the chromosome: The first approach was based on the recently determined physical map of P. aeruginosa PAO (55); in these experiments algU was used as a probe for Southern hybridization analysis of SpeI fragments separated by pulsed field gel electrophoresis. The second approach was to map algU via F116L transduction; in this case we took the advantage of having a strain (PAO670) with the algU gene on the chromosome tagged with the $Tc^r$ cassette and monitored the coinheritance of pruAB with $Tc^r$.

Figure 5:
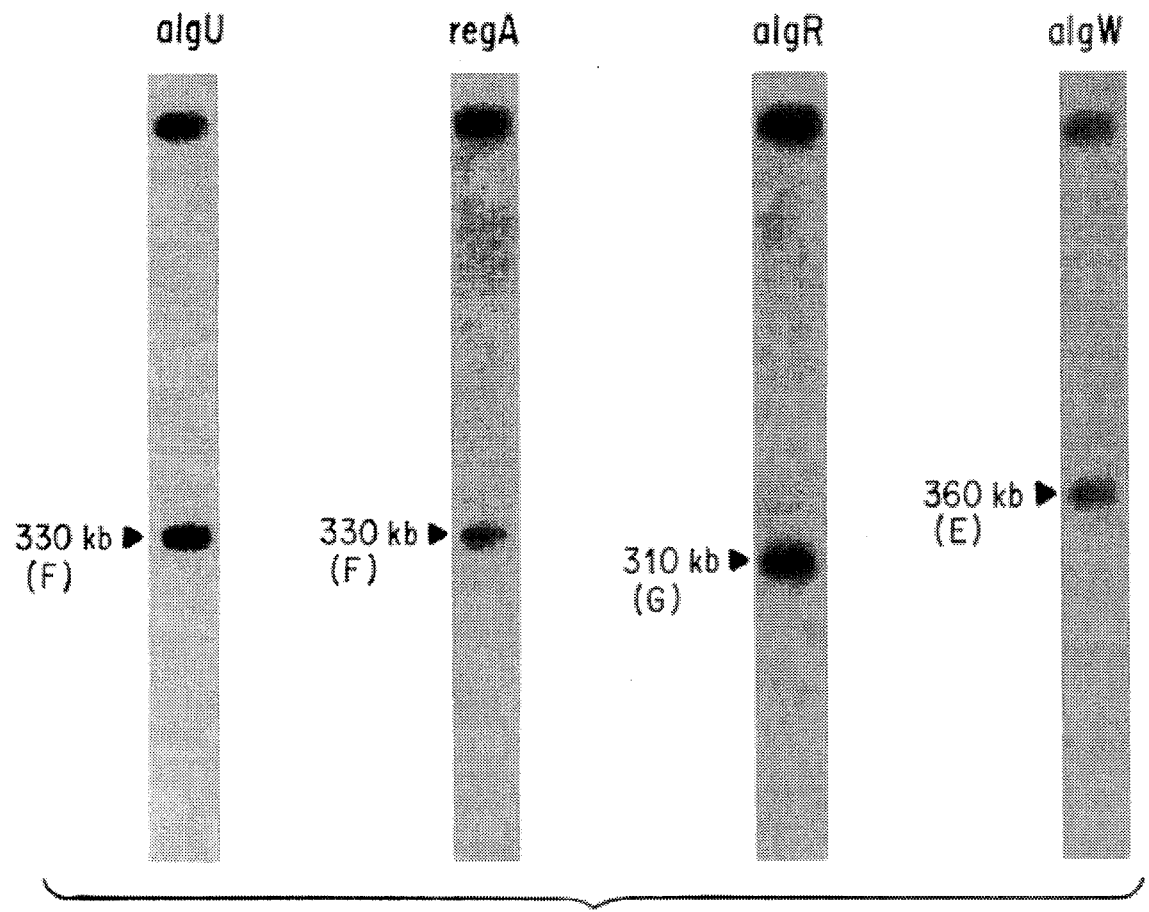
FIG. 5. Physical mapping of algU on the chromosome of P. aeruginosa. Shown is a Southern blot hybridization of various probes (indicated above each strip) with PAO1 DNA digested with SpeI, fragments separated on agarose gel by pulsed-field electrophoresis, and blotted onto a membrane. The radiolabeled probes were hybridized, autoradiograms obtained, probes stripped of the filter and checked for completeness of the process, and the blot reprobed with a different gene. Probes: algU; regA, a gene that regulates toxin A synthesis (30); algR, a response regulator controlling algD transcription (10); algW, a 6 kb HindIII-NsiI fragment from pMO011809, that also affects mucoidy (see Results) (55). Horizontal bar, chromosomal DNA retained within the well hybridizing with all probes. The SpeI fragments hybridizing to corresponding probes are indicated by triangles, and their size and designation (letters in parenthesis), based on the physical map (SpeI) of the P. aeruginosa chromosome, indicated.

The results of the Southern blot analyses with SpeI digested PAO chromosome subjected to separation by pulse field gel electrophoresis are illustrated on a gel in FIG. 5. As explained in the figure legend, several consecutively applied probes were used to confirm identification of the SpeI fragments. The algU gene hybridized to the 330 kb SpeI fragment (#6, F) known to carry two genetic markers linked to muc-2 and muc-22, viz. pur-70 at 66 min, and pruAB at 67.5 min (55). This indicated that algU may be close to the muc-2 and muc-22 markers. To explore this possibility, cotransducibility of pruAB with algU::$Tc^r$ was tested. The results of transductional crosses between PAO670 [algU::$Tc^r$ on the chromosome of PAO568 (muc-2)] and PAO964 (pru-354), a mutant in pruAB which cannot grow on proline as the sole carbon and nitrogen source, revealed a high degree of coinheritance of pruAB with algU::$Tc^r$ (Table 5).

TABLE 5

Cotransduction of algU and pruAB[a].

| Donor × Recipient | Selected marker[b] | % coinheritance of the unselected marker[c] | |
|---|---|---|---|
| | | $Tc^r$ | Mucoidy |
| PAO670 × PAO964 | pru-354[+] | 20.3 | 0 (<0.3%) |
| PAO670 × PAO540 | hisI[+] | 0 (<0.25%) | 0 (<0.25%) |

[a]F116L transduction was performed using an algU::$Tc^r$ derivative of PAO568 (muc-2) (strain PAO670) as the donor, and PAO964 (pru-354) or PAO540 (cys-5605 his-5075 argA171) as recipients. PAO670 is nonmucoid due to the inactivation of algU by the insertion of $Tc^r$ cassette. PAO964 and PAO540 are nonmucoid.
[b]pru-354 is a mutant allele of pruAB (44). PAO964 (pru-354) cannot grow on proline as the sole carbon and nitrogen source. The selection was performed for pruAB[+] or hisI as described in Materials and Methods.
[c]pruAB[+] transductants (300 colonies) and hisI transductants (400 colonies) were tested for coinheritance of $Tc^r$. $Tc^r$ in transduction crosses originates from algU::$Tc^r$ on the PAO670 chromosome. No strain displayed mucoid character in at least two independent transduction experiments. In a reciprocal experiment, in which $Tc^r$ was the selected marker, a 50% coinheritance of pruAB[+] with $Tc^r$ was observed (not shown).

The % coinheritance of $Tc^r$ with pruAB corresponded closely to the values previously reported for muc-2 and muc-22 (20–49%) (23,25). In a control experiment, no coinheritance of hisI and $Tc^r$ was observed using the same transducing phage lysates (Table 5). Significantly, no mucoid transductants (expected from the transfer of muc-2) among over 700 colonies examined were observed in these crosses regardless whether the selection was for pru[+] or $Tc^r$. This was in sharp contrast with the results obtained with the recipient strain PAO964 and the donor strain PAO568 (muc-2; the strain parental to PAO670). Normally, 49% of the pru[+] colonies are mucoid in transductions involving PAO568 and PAO964 (23,25). Although PAO568 in our hands had the capacity to transfer the muc-2 marker conferring mucoidy upon the recipient cells, its algU::$Tc^r$ derivative PAO670 completely lost this ability. This effect could be attributed to the insertional inactivation of algU in PAO670. These results indicate that algU is in the close vicinity of the muc loci represented by muc-2 and muc-22 and may even be allelic with these determinants.

AlgU shows sequence similarity with SpoOH, a sigma factor required for developmental processes in Bacillus subtilis. In order to gain information about the nature and possible function of genetic elements within the algU region, the nucleotide sequence of the DNA region from the endpoint of the deletion ?U4/76 (the last 5' deletion positive for suppression of mucoidy and synthesis of P27) and extending through one of the EcoRV sites used for insertional inactivation of algU was determined (FIG. 6). An open reading frame was identified within the region defined as algU by deletion and functional mapping. This sequence contained translational initiation signals, conformed with Pseudomonas codon usage (63), and was in the direction of transcription determined in T7 expression studies. When a global homology search was performed using the translated sequence of algU with GenBank and NBRF databases, two known proteins showed statistically significant similarity with AlgU: SpoOH from *B. licheniformis* and *B. subtilis*. SpoOH is dispensable for growth, and is primarily required for initiation of sporulation and other developmental processes (competence) in *B. subtilis* (20,62). The sequence similarity observed (24.9% identity over the entire length of both sequences, and the optimized score of 155), although limited, was equivalent to the extent of similarity of sigma$^H$ to other known sigma factors (ranging between 22% and 31% identity with optimized scores between 113 and 145) (20). All regions noted in several sequence compilations and alignments of sigma factors (29,41) were represented in the regions of homology between SpoOH and AlgU. The predicted pI of AlgU was 5,315, similar to the pI of SpoOH (5.052–5.146). A relatively low pI is characteristic of sigma factors (45) and is known to cause anomalous mobility of several members of this class of proteins during SDS-PAGE (45). This may help explain a discrepancy in the observed electrophoretic mobility corresponding to 27.5 kDa and predicted $M_r$ of AlgU from the sequence (22,194 Da) which is in the range of discrepancies reported for several sigma factors (45). *B. subtilis* sigma$^H$ shows electrophoretic mobility corresponding to 30 kDa, while its predicted $M_r$ is 25,331 (5). The pertinent parts of the following references for this example are incorporated by reference herein.

REFERENCES

1. Allen, L. N., and R. S. Hanson. 1985. Construction of broad host range cloning vectors: identification of genes necessary for growth of Methylobacterium organophilum on methanol. J. Bacteriol. 161:955–962.
2. Anwar, H., J. L. Strap, and J. W. Costerton. 1992. Establishment of aging biofilms: possible mechanism of bacterial resistance to antimicrobial therapy. Antimicrob. Agents Chemother. 36:1347–1351.
3. Ausubel, F. M., R. Brent, R. E. Kingston, D. D. Moore, J. G. Seidman, J. A. Smith, and K. Struhl. 1989. Current protocols in molecular biology. John Wiley & Sons, Inc., New York.
4. Barry, C. E. III, S. F. Hayes, and T. Hackstadt. 1992. Nucleoid condensation in *Escherichia coli* that express a chlamidial histone homolog. Science 256:377–379.
5. Carter, H. L., III, and C. P. Moran, Jr. 1986. New RNA polymerase_factor under spo0 control in *Bacillus subtilis*. Proc. Natl. Acad. Sci. USA 83:7438–9442.
6. Chater, K., C. J. Bruton, K. A. Plaskitt, M. J. Buttner, C. Mendex, and J. D. Helmann. 1989. The developmental fate of S. coelicolor hyphae depends upon a gene product homologous with the mobility_factor of *B. subtilis*. Cell 59:133–143.
7. Costerton, J. W., K.-J. Cheng, G. G. Geesey, T. I. Ladd, J. C. Nickel, M. Dasgupta, T. J. Marrie. 1987. Bacterial biofilms in nature and disease. Ann. Rev. Microbiol. 41:435–464.
8. Costerton, J. W., J. Lam, K. Lam, and R. Chan. 1983. The role of the microcolony mode of growth in the pathogenesis of *Pseudomonas aeruginosa* infections. Rev. Infect. Dis. 5:S867–S873.
9. Deretic, V., S. Chandrasekharappa, J. F. Gill, D. K. Chatterjee, and A. M. Chakrabarty. 1987. A set of cassettes and improved vectors for genetic and biochemical characterization of Pseudomonas genes. Gene 57:61–72.
10. Deretic, V., R. Dikshit, W. M. Konyecsni, A. M. Chakrabarty, and T. K. Misra. 1989. The algR gene, which regulates mucoidy in Pseudomonas aeruginosa, belongs to a class of environmentally responsive genes. J. Bacteriol. 171:1278–1283.
11. Deretic, V., J. F. Gill, and A. M. Chakrabarty. 1987. Gene algD coding for GDPmannose dehydrogenase is transcriptionally activated in mucoid *Pseudomonas aeruginosa*. J. Bacteriol. 169:351–358.
12. Deretic, V., J. R. W. Govan, W. M. Konyecsni, and D. W. Martin. 1990. Mucoid Pseudomonas aeruginosa in cystic fibrosis: mutations in the muc loci affect transcription of the algR and algD genes in response to environmental stimuli. Mol. Microbiol. 4:189–196.
13. Deretic, V., N. S. Hibler, and S. C. Holt. 1992. Immunocytochemical analysis of AlgP ($H_p1$), a histonelike element participating in control of mucoidy in *Pseudomonas aeruginosa*. J. Bacteriol. 174:824–831.
14. Deretic, V., and W. M. Konyecsni. 1989. Control of mucoidy in *Pseudomonas aeruginosa:* transcriptional regulation of algR and identification of the second regulatory gene, algQ. J. Bacteriol. 171:3680–3688.
15. Deretic, V., and W. M. Konyecsni. 1990. A prokaryotic regulatory factor with a histone H1-like carboxy-terminal domain: clonal variation of repeats within algP, a gene involved in regulation of mucoidy in *Pseudomonas aeruginosa*. J. Bacteriol. 172:5544–5554.
16. Deretic, V., W. M. Konyecsni, C. D. Mohr, D. W. Martin, and N. S. Hibler. 1989. Common denominators of promoter control in Pseudomonas and other bacteria. Bio/Technology 7:1249–1254.
17. Deretic, V., J. H. J. Leveau, C. D.Mohr, and N. S. Hibler. 1992. In vitro phosphorylation of AlgR, a regulator of mucoidy in *Pseudomonas aeruginosa*, by a histidine protein kinase and effects of small phospho-donor molecules. Mol. Microbiol. 6:2761–2767.
18. Deretic, V., C. D. Mohr, and D. W. Martin. 1991. Mucoid *Pseudomonas aeruginosa* in cystic fibrosis: signal transduction and histone-like elements in the regulation of bacterial virulence. Mol. Microbiol. 5:1557–1583.
19. Dubnau, D. 1991. The regulation of genetic competence in *Bacillus subtilis*. Mol. Microbiol. 5:11⁻18.
20. Dubnau, E., J. Weir, G. Nair, L. Carter III, C. Moran, Jr., and I. Smith. Bacillus sporulation gene spo0H codes for _$^{30}$ (_$^4$). J. Bacteriol. 170:1054–1062 . . . F-4.
21. Figurski, D. H., and D. R. Helinski. 1979. Replication of an origin-containing derivative of plasmid RK2 dependent on a plasmid function provided in trans. Proc. Natl. Acad. Sci. USA 76:1648–1652.
22. Flynn, J. L., and D. E. Ohman. 1988. Cloning of genes from mucoid *Pseudomonas aeruginosa* which control spontaneous conversion to the alginate production phentotype. J. Bacteriol. 170:1452–1460.
23. Fyfe, J. A. M. 1985. Studies on some unusual characteristics expressed by Pseudomonas aeruginosa associated with chronic respiratory infections. Ph.D. Thesis. University of Edinburgh.
24. Fyfe, J. A. M., and J. R. W. Govan. 1980. Alginate synthesis in mucoid *Pseudomonas aeruginosa:* a chromosomal locus involved in control. J. Gen. Microbiol. 119:443–450.
25. Fyfe, J. A. M., and J. R. W. Govan. 1983. Synthesis, regulation and biological function of bacterial alginate. In Progress in inductrial microbiology, vol. 18 (Bushell, M. E., ed.). Elsevier, Amsterdam, pp. 45–83.
26. Goldberg, J. B., J. Won, and D. E. Ohman. 1990. Precise excision and instability of the transposon Tn5 in *Pseudomonas aeruginosa*. J. Gen. Microbiol. 136:789–796.
27. Govan, J. R. W. 1988. Alginate biosynthesis and other unusual characteristics associated with the pathogenesis of

*Pseudomonas aeruginosa* in cystic fibrosis. p. 67–96. In E. Griffiths, W. Donachie, and J. Stephen, (eds.), Bacterial infections of respiratory and gastrointestinal mucosae. IRL Press, Oxford.

28. Govan, J. R. W., and G. S. Harris. 1986. *Pseudomonas aeruginosa* and cystic fibrosis: unusual bacterial adaptation and pathogenesis. Microbiol. Sci. 3:302–308.

29. Helmann, J. D., and M. J. Chamberlin. 1988. Structure and function of bacterial sigma factors. Ann. Rev. Biochem. 57:839–872.

30. Hindahl, M. S., D. W. Frank, A. Hamood, and B. H. Iglewski. 1988. Characterization of a gene that regulates toxin A synthesis in *Pseudomonas aeruginosa*. Nucleic Acids Res. 16:5699.

31. Holloway, B. W. 1955. Genetic recombination in *Pseudomonas aeruginosa*. J. Gen. Microbiol. 23:572–581.

32. Ishimoto, K., and S. Lory. 1989. Formation of pilin in *Pseudomonas aeruginosa* requires the alternative factor (RpoN) of RNA polymerase. Proc. Natl. Acad. Sci. USA 86:1954–1957.

33. Kato, J., and A. M. Chakrabarty. 1991. Purification of the regulatory protein AlgR1 and its binding in the far upstream region of the algD promoter in *Pseudomonas aeruginosa*. Proc. Natl. Acad. Sci. USA 88:1760–1764.

34. Kato, J., T. K. Misra, and A. M. Chakrabarty. 1990. AlgR3, a protein resembling eukaryotic histone H1, regulates alginate synthesis in *Pseudomonas aeruginosa*. Proc. Natl. Acad. Sci. USA 87:2887–2891.

35. Kimbara, K., and A. M. Chakrabarty. 1989. Control of alginate synthesis in *Pseudomonas aeruginosa*: regulation of the algR1 gene. Biochem. Biophys. Res. Com. 164:601–608.

36. Knutson, C. A., and A. Jeanes. 1976. A new modification of the carbazole reaction: application to heteropolysaccharides. Anal. Biochem. 24:470–481.

37. Konyecsni, W. M., and V. Deretic. 1989. Broad-host-range plasmid and M13 bacteriophage-derived vectors for promoter analysis in *Escherichia coli* and *Pseudomonas aeruginosa*. Gene 74:375–386.

38. Konyecsni, W. M., and V. Deretic. 1990. DNA sequence and expression analysis of algP and algQ, components of the multigene system transcriptionally regulating mucoidy in *Pseudomonas aeruginosa*: algP contains multiple direct repeats. J. Bacteriol. 172:2511–2520.

39. Krieg, D., R. Helmke, V. German, and J. Mangos. 1988. Resistance of mucoid *Pseudomonas aeruginosa* to opsonic phagocytosis by alveolar macrophages in vitro. Infect. Immun. 56:3173–3179.

40. Krishnapillai. V. 1971. A novel transducing phage. Its role in recognition of a possible new host-controlled modification system in *Pseudomonas aeruginosa*. Mol. Gen. Genet. 114:134–143.

41. Lonetto, M., M. Gribskov, and C. A. Gross. 1992. The $\sigma^{70}$ family: sequence conservation and evolutionary relationships. J. Bacteriol. 174:3843–3849.

42. Losick, R., P. Youngman, and P. J. Piggot. 1986. Genetics of endospore formation in *Bacillus subtilis*. Ann. Rev. Genet. 20:625–669.

43. MacGeorge, J., V. Korolik, A. F. Morgan, V. Asche, and B. W. Holloway. 1986. Transfer of a chromosomal locus responsible for mucoid colony morphology in *Pseudomonas aeruginosa* isolated from cystic fibrosis patients to *P. aeruginosa* PAO. J. Med. Microbiol. 21:331–336.

44. Meile, L., L. Soldati, and T. Leisinger. 1982. Regulation of proline catabolism in *Pseudomonas aeruginosa* PAO. Arch. Microbiol. 132:189–193.

45. Merrick, M. J. and J. R. Gibbins. 1985. The nucleotide sequence of the nitrogen-regulation gene ntrA of *Klebsiella pneumoniae* and comparison with conserved features in bacterail RNA polymerase sigma factors. Nucleic Acids Res. 13:7607–7620.

46. Miller, J. F., J. J. Mekalanos, and S. Falkow. 1989. Coordinate regulation and sensory transduction in the control of bacterial virulence. Science 243:916–922.

47. Mohr, C. D. and V. Deretic. 1990. Gene-Scrambling Mutagenesis: Generation and Analysis of Insertional Mutations in the Alginate Regulatory Region of *Pseudomonas aeruginosa*. J. Bacteriol. 172:6252–6260.

48. Mohr, C. D. M., N. S. Hibler, and V. Deretic. 1991. AlgR, a response regulator controlling mucoidy in *Pseudomonas aeruginosa*, binds to the FUS sites of the algD promoter located unusually far upstream from the mRNA start site. J. Bacteriol. 173:5136–5143.

49. Mohr, C. D., J. H. J. Leveau, D. P. Krieg, N. S. Hibler, and V. Deretic. 1992. AlgR-binding sites within the algD promoter make up a set of inverted repeats separated by a large intervening segment of DNA. J. Bacteriol. 174:000–000.

50. Mohr, C. D., D. W. Martin, W. M. Konyecsni, J. R. W. Govan, S. Lory, and V. Deretic. 1990. Role of the far-upstream sites of the algD promoter and the algR and rpoN genes in environmental modulation of mucoidy in *Pseudomonas aeruginosa*. J. Bacteriol. 172:6576–6580.

51. Ohman, D. E., J. B. Goldberg, and J. L. Flynn. 1990. Molecular analysis of the genetic switch activating alginate production. In: S. Silver, A.M. Chakrabarty, B. Iglewski, and S. Kaplan (eds.), Pseudomonas biotransformations, pathogenesis, and evolving biotechnology. American Society for Microbiology, Washington, D.C.

52. Pearson, W. R., and D. J. Lipman. 1988. Improved tools for biological sequence comparison. Proc. Natl. Acad. Sci. USA 85:2444–2448.

53. Predich, M., N. Gopal, and I. Smith. 1992. *Bacillus subtilis* early sporulation genes kinA, spoOF, and spoOA are transcribed by the RNA polymerase containing $\sigma^H$. J. Bacteriol. 174:2771–2778.

54. Rappuoli, R., B. Arico, and V. Scarlato. 1992. Thermoregulation and reversible differentiation in Bordetella: a model for pathogenic bacteria. Mol. Microbiol. 6:2209–2211.

55. Ratnaningsih, E., S. Dharmsthiti, V. Krishnapillai, A. Morgan, M. Sinclair, and B. W. Holloway. 1990. A combined physical and genetic map of *Pseudomonas aeruginosa* PAO. J. Gen. Microbiol. 136:2351–2357.

56. Sadoff, H. L. 1975. Encystment and germination in Azotobacter vinelandii. Bacteriol. Rev. 39:516–539.

57. Selvaraj, C., Y. C. Fong, and V. N. Iyer. A portable DNA sequence carrying the cohesive site (cos) of bacteriophage and the mob (mobilization) region of the broad-host-range plasmid RK2: a module for the construction of new cosmids. Gene 32:235–241.

58. Simon, R., V. Priefer, and A. Puhler. 1983. A broad host range mobilization system for in vivo genetic engineering: transposon mutagenesis in gram negative bactera. Bio/Technology 1:784–791.

59. Shortridge, V. D., M. L. Pato, A. I. Vasil, and M. L. Vasil. 1991. Physical mapping of virulence-associated genes in *Pseudomonas aeruginosa* by transverse alternating-field electrophoresis. Infect. Immun. 59:3596–3603.

60. Tabor, S., and C. C. Richardson. A bacteriophage T7 RNA polymerase/promoter system for controlled expression of specific genes. Proc. Natl. Acad. Sci. USA 82:1074–1078.

61. Stock, J. B., A. J. Ninfa, and A.M. Stock. 1989. Protein phosphorylation and the regulation of adaptive responses in bacteria. Microbiol. Rev. 53:450–490.

62. Tatti, K. M., H. L. Carter III, A. Moir, and C. P. Moran, Jr. 1989. Sigma H-directed transcription of citG in *Bacillus subtilis*. J. Bacteriol. 171:5928–5932.
63. West, S. E., and B. H. Iglewski. 1988. Codon usage in *Pseudomonas aeruginosa*. Nucleic Acids Res. 16:9323–9335.
64. Woodruff, W. A., D. J. Hassett, and D. E. Ohman. 1992. Sequence analysis of *Pseudomonas aeruginosa* DNA containing the alginate gene algT revealed the adjacent gene nadB encoding aspartate oxidase. Abstracts of the General Meeting, New Orleans 1992, American Society for Microbiology, Washington D.C., p. 103.
65. Wozniak, D. J., and D. E. Ohman. 1991. *Pseudomonas aeruginosa* AlgB, a two-component response regulator of the NtrC family, is required for algD transcription. J. Bacteriol. 173:1406–1413.

EXAMPLE 2

Differentiation of *Pseudomonas aeruginosa* into the Alginate Producing Form: Inactivation of mucB Causes Conversion to Mucoidy This example further characterizes genes within the chromosomal region at 67.5 min which play a critical role in determining the mucoid status of *P. aeruginosa*. Two new genes within this locus, mucA and mucB, have been identified, characterized, and demonstrated to participate in the control of mucoidy.

EXPERIMENTAL PROCEDURES

References cited herein are listed at the end of the specification.
Bacterial strains, plasmids and growth conditions. All strains of *Pseudomonas aeruginosa* used in this study are derivatives of the standard genetic strain PAO1. PAO671 was generated by the insertional inactivation of mucB (mucB::Tc$^r$) on the chromosome of the nonmucoid parental strain PAO381 (FP2$^+$ leu-38 mucA$^+$ mucB$^+$; Fyfe and Govan, 1980). This was accomplished using a previously described procedure for allele replacement (Martin et al., 1993). A 2.4 HindIII-EcoRI fragment (U4/76) was inserted into pUC12. A BglII fragment containing the Tc$^r$ cassette was cloned into the unique BglII site within the mucB open reading frame. Next a 1.4-kb EcoRI fragment with mob from pCMobA (Mohr and Deretic 1990; Selvaray et al., 1984) was inserted into a unique EcoRI site resulting in pDMB100. This plasmid was transferred by triparental conjugations into PAO381 to generate PAO671, and additionally into three other nonmucoid PAO strains. Exconjugants were selected on PIA supplemented with tetracycline and double crossovers were identified as Tc$^r$ and Cb$^s$. In all cases, Tc$^r$ Cb$^s$ exconjugants were mucoid, while Tc$^r$ Cb$^r$ (single crossovers) were nonmucoid. Gene replacements in Tc$^r$ Cb$^s$ strains (all mucoid) were verified by Southern blot analysis.
*P. aeruginosa* was grown on LB and Pseudomonas Isolation agar (PIA, Difco). Antibiotic supplements for *P. aeruginosa* were 300 µg/ml tetracycline for PIA, 50 µg/ml of tetracycline for LB and 300 µg/ml carbenicillin for all media. *Escherichia coli* was grown on LB supplemented with tetracycline (10 µg/ml), ampicillin (40 µg/ml) and kanamycin (25 µg/ml) when required. All incubation were at 37° C.
Nucleic acid manipulations and recombinant DNA techniques. All recombinant DNA manipulations and Southern blot analysis were carried out using standard procedures (Ausubel et al., 1989; Martin et al., 1993). DNA sequencing was carried out using the United States Biochemical Sequenase kit with 7-deaza GTP.
Labeling and detection of the mucB gene product. The gene product of mucB was specifically labeled and expressed in *E. coli* using a temperature-inducible T7 RNA polymerase/promoter expression system (plasmid vectors pT7-6 or pT7-5 and T7 RNA polymerase encoded by pGP1-2) (Tabor and Richardson 1985). Nascent polypeptides were labeled with [$^{35}$S]methionine and [$^{35}$S]cysteine (Expre$^{35}$S$^{35}$S protein labeling mix; 1,000 Ci/mmol; DuPont NEN). Proteins were separated on a sodium dodecyl sulfate (SDS)-12% polyacrylamide gel. $^{14}$C-labeled methylated proteins (Amersham) were used as molecular weight standards. Gels were fixed in 10% acetic acid, washed with H$_2$O, impregnated with 1M salicylic acid, and bands representing radiolabeled peptides were detected by autofluorography at −70° C.
Phenotypic scoring, enzyme assays and alginate measurements. Suppression of mucoidy by plasmid-borne genes was monitored on PIA plates, and the phenotypic appearance of the colonies was scored as mucoid or nonmucoid. Alginate was assayed as previously described (Knutson and Jeanes, 1976). Various deletion products of the region containing the genes algU, mucA, and mucB were placed in the broad host range vector pVDZ'2 (Martin et al., 1993) and introduced into PAO568 and PAO581 to test their ability to suppress mucoidy. The plasmid pPAOM3 (Cb$^r$; Konyecsni and Deretic 1988), containing an algD::xylE transcriptional fusion, was introduced into PAO671 carrying mucB::Tc$^r$ and the parental strain PAO381 (Table 6) by triparental conjugation (Konyecsni and Deretic, 1988). Cell-free sonic extracts were assayed for catechol 2,3-dioxygenase (CDO) activity using previously described methods (Konyecsni and Deretic 1988). The activity was monitored in 50 mM phosphate buffer (pH 7.5)-0.33 mM catechol by following the increase of A$_{375}$ in a Shimadzu UV160 spectrophotometer. The molar extinction coefficient of the reaction product, 2-hydroxymuconic semialdehyde, is 4.4×10$^4$ at 375 nm. 1 unit of CDO is defined as the amount of enzyme that oxidizes 1 µmol of catechol per min at 24° C.

RESULTS

Figure 7:
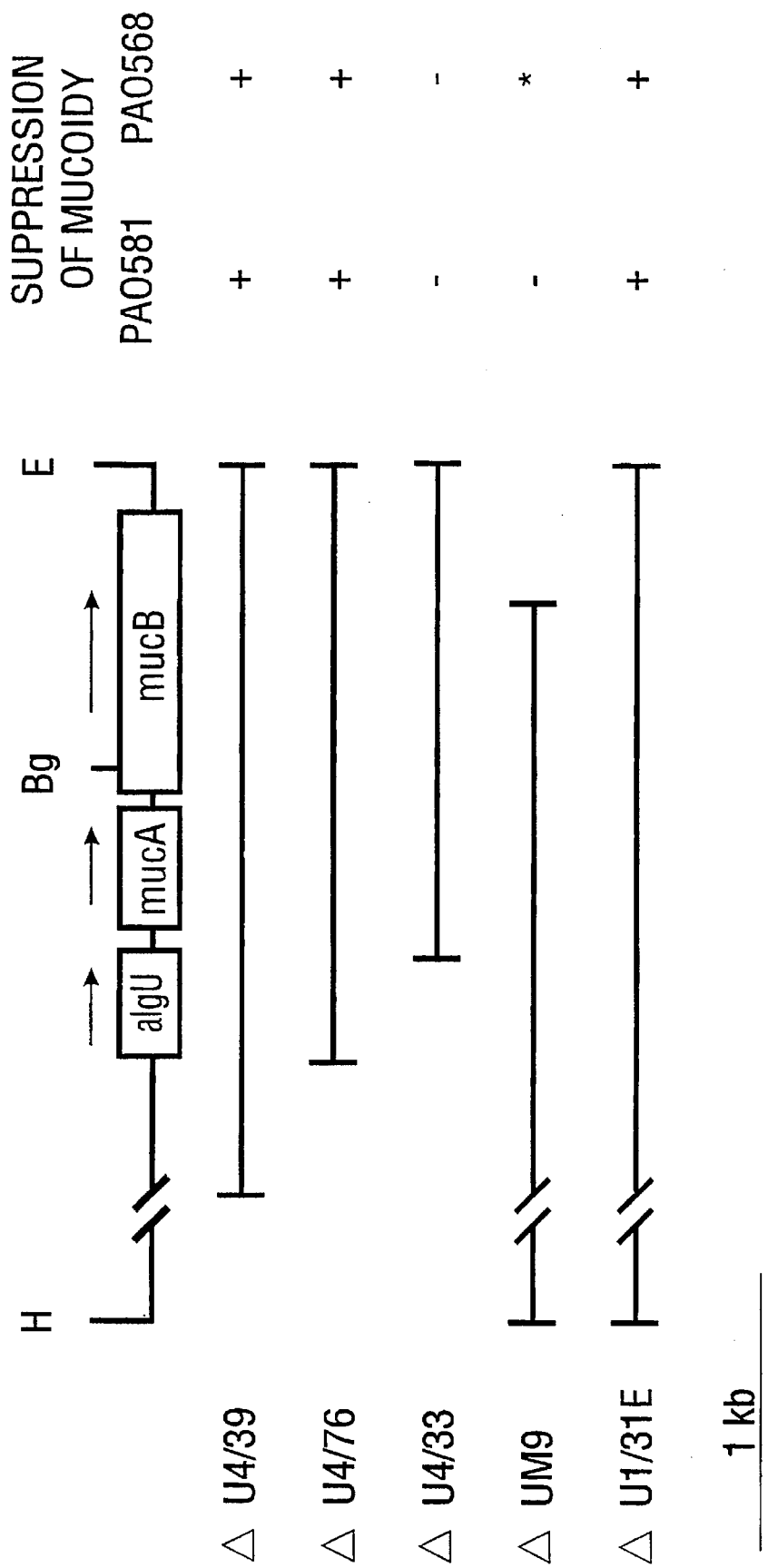
FIG. 7. The algU, mucA, mucB regulatory region at 67.5 min of the P. aeruginosa chromosome and the results of suppression of mucoidy. Relative positions, orientation (arrows), and size of genes are shown. Lines under the map represent different inserts (designations given on the left side) cloned in the broad host range plasmid pVDZ'2. The effect on mucoidy (+, suppression; –, no effect, viz. the strain remains mucoid; *, strain is nonmucoid after 24 h but becomes mucoid after several days) was scored after conjugal transfer of clones into PAO581 (muc-25) and PAO568 (muc-2). The genomic HindIII-EcoRI fragment has 6 kb; (interrupted lines, fragments are not drown in their entirety). Bg, BglII, E, EcoRI; H, HindIII.

Complementation of muc-25 requires two genes downstream of algU. The present inventors have discovered that the chromosomal muc mutations can be suppressed to nonmucoidy (Martin et al., 1993). This can be accomplished by in trans complementation with a cosmid clone and its derivatives carrying DNA from a nonmucoid PAO strain (Martin et al., 1993). It has also been shown that this suppression activity was at the level of reducing algD transcription (Martin et al., 1993). The region needed for complementation includes algU, but this process also requires additional sequences downstream of algU (Martin et al., 1993). These studies have also indicated the presence of at least one additional gene, termed mucA, immediately following algU, which encodes a polypeptide (P20) with an apparent M$_r$ of 20 kDa (Martin et al., 1993). algU and mucA are necessary to exert detectable suppression of mucoidy in the PAO568 (muc-2) strain (Fyfe and Govan, 1980). Finer analyses indicated that a region further downstream of mucA was also needed to completely abrogate mucoidy in this strain (FIG. 7). Moreover, another isogenic mucoid strain, PAO581, carrying a different muc mutation (muc-25) known to map close to muc-2, was not affected by the DNA fragment containing only algU and mucA unless downstream sequences were included. The present inventors further defined this additional region. The results of these experiments are shown in FIG. 7. Based on the size of additional DNA required for the suppression activity, it seemed likely that there was another gene, located downstream of the mucA gene, that was needed for suppression of mucoidy in PAO581. To test this hypothesis we first determined whether a polypeptide product encoded by this DNA region could be detected. The results of these studies are shown in FIG. 8. A polypeptide with an apparent $M_r$ of 32.8 kDa (P33) was encoded by the insert required for the suppression of the muc-25 mutation. No polypeptide product was observed when the same inserts were expressed in the opposite direction. However, P33 was expressed relatively poorly when compared to algU and mucA (not shown) (Martin et al., 1993). The gene encoding P33 was designated mucB.

Complete nucleotide sequence of the mucA and mucB genes. In order to further characterize the mucA and mucB genes, the complete nucleotide sequence of this region from the prototype PAO strain PAO1 (nonmucoid), parental to PAO381 and its mucoid derivatives PAO568 and PAO581, was determined. The sequence of algU has been reported previously (Martin et al., 1993). The assignment of open reading frames for mucA and mucB in this region was facilitated by protein expression and other analyses. The only two open reading frames compatible with: (i) the order of genes (mucA followed by mucB); (ii) direction of transcription; (iii) apparent $M_r$ of gene products (P20 and P33); (iv) the endpoints of deletions encroaching on the mucB open reading frame that abrogate the suppression activity in PAO581; and (v) conforming with the codon usage typical of Pseudomonas (West and Iglewski, 1988) are shown in FIG. 9A, 9B, and 9C. The mucA open reading frame, encoding a polypeptide with predicted $M_r$ of 20,997, immediately follows algU. The mucB open reading frame, within the region necessary for suppression of mucoidy in PAO581 (FIG. 9A, 9B, and 9C) encodes a polypeptide with predicted $M_r$ of 34,471 kDa. To further confirm the correct assignment of the genes, this same region was cloned using PCR from several different strains, including PAO381, and in each case the complete nucleotide sequence was determined in multiple PCR clones confirming the one presented in FIG. 9A, 9B, and 9C.

Insertional inactivation of mucB on the chromosome of the nonmucoid strain PAO381 results in mucoid phenotype. Any explanation of the requirement for all three genes (algU, mucA, and mucB) for suppression of mucoidy must take into account that algU plays a positive regulatory role in algD expression, possibly as the sigma factor required for mRNA initiation at the algD promoter (Martin et al., 1993). One of the models compatible with this function of algU in conjunction with the requirement for mucA and mucB (from a nonmucoid strain) to complement muc mutations and suppress mucoidy, is that mucA and mucB counteract the activity of algU and are needed for the maintenance of nonmucoid phenotype. If this is the case, then inactivation of mucB on the chromosome of *P. aeruginosa* should result in the mucoid phenotype.

Figure 10A:
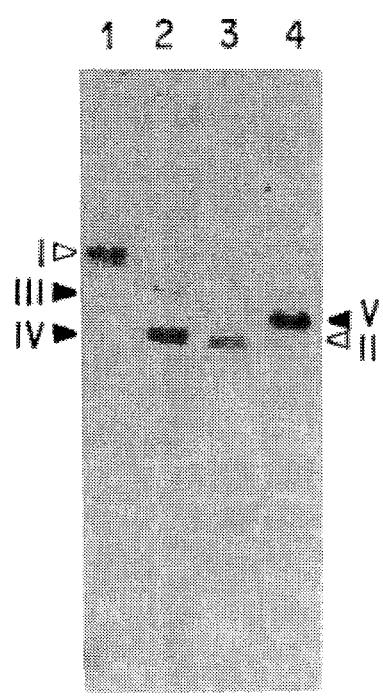
FIG. 10A and FIG. 10B. Inactivation of mucB on the chromosome of PAO381 resulting in conversion to mucoidy. Top panel shows Southern blot analysis of the gene replacement of mucB with the insertionally inactivated mucB::Tc$^r$ allele. PAO381 is the parental nonmucoid strain (lanes 1 and 3); PAO671 (mucB::Tc$^r$) is its mucoid derivative (lanes 2 and 4). Restriction enzyme digests of chromosomal DNA: lanes 1 and 2, BamHI; 3 and 4, EcoRI. Open triangles indicate bands corresponding to the fragments from the parental strain PAO381 hybridizing to the probe 4/76. Filled triangles indicate positions of bands hybridizing to the same probe in PAO671. Roman numerals denote corresponding fragments indicated on the scheme underneath the blot. Scheme shows an allelic exchange via double crossover event between the plasmid pDMB100 and the PAO381 chromosome. Open box, algU; stippled box, mucA; filled box, mucB; hatched box, Tc$^r$ cassette. Ap$^r$(Cb$^r$), ampicillin (carbenicillin resistance) encoded by the plasmid moiety. mob, mobilization site. B, BamHI; other restriction sites as in FIG. 7.
Figure 10B:
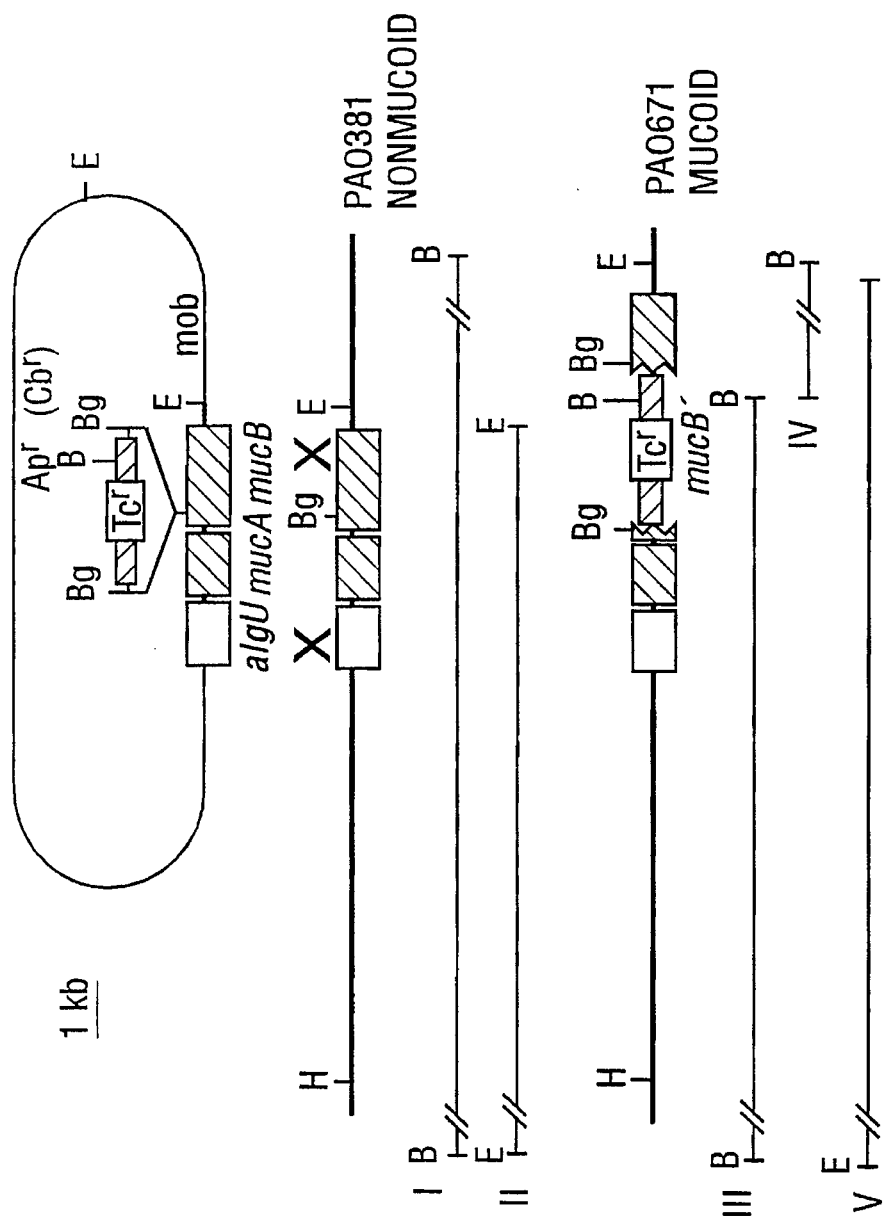

To test this hypothesis we inactivated mucB on the chromosome of the nonmucoid strain PAO381. This strain is parental to the mucoid derivatives PAO568 (muc-2), and PAO581 (muc-25) that have muc mutations mapping in the same chromosomal region (67.5 min) as the algU-mucAB cluster (Fyfe and Govan, 1980; 1983; Martin et al., 1993). Thus, PAO381 is capable of conversion to mucoidy via mutations in the muc genes. To inactivate mucB, the algU-mucAB cluster was first cloned on pUC12. The conveniently located BglII site (FIG. 9) within the coding region of mucB was used to insert a $Tc^r$ cassette (Totten, et al., 1990), resulting in the disruption of mucB, as described in Experimental Procedures. To this construct was added a fragment containing mob functions (to facilitate its mobilization into *P. aeruginosa*), resulting in the plasmid pDMB100. Since pUC12 and its derivative pDMB100 cannot replicate in Pseudomonas, upon a transfer of this plasmid into *P. aeruginosa* via triparental conjugation (see Experimental Procedures), any $Tc^r$ exconjugants must carry this marker integrated on the chromosome. This can occur via homologous recombination involving the algU-mucAB region through single crossover or double crossover events. In the case of single crossovers, the exconjugants are expected to be merodiploids, and should also display $Cb^r$ ($Ap^r$; encoded by the vector moiety); in the case of double crossovers, a true gene replacement is expected to take place with the vector moiety of the plasmid being lost, and thus the resulting strains should be sensitive to carbenicillin ($Cb^s$). Of 129 $Tc^r$ *P. aeruginosa* exconjugants obtained from 4 independent crosses between *E. coli* JM83 harboring pDMB100 and PAO381, 28% of exconjugants were $Cb^r$, indicative of a single crossover event. As expected, all such strains were nonmucoid, since they were merodiploids, and contained a functional copy of mucB. These strains were indistinguishable from the parental strain PAO381. In contrast, all $Tc^r$ exconjugants that were $Cb^s$ (72% of total $Tc^r$ exconjugants), thus indicative of double crossover events, became mucoid. Thus, a complete and stable conversion to mucoidy was achieved by inactivating mucB on the chromosome of a previously nonmucoid strain. A true gene replacement event of mucB with mucB::$Tc^r$ on the chromosome of such strains was further confirmed by Southern blot hybridization (FIG. 10A and 10B).

To determine whether inactivation of mucB resulted in transcriptional activation of algD, one such mucB::$Tc^r$ strain (PAO671) was further examined. A plasmid containing algD-xylE transcriptional fusion was introduced into PAO671 and the levels of algD transcription in the parental strain PAO381 (mucB$^+$) and its mucoid derivative PAO671 (mucB::$Tc^r$) were compared. The results of these experiments indicated a 26-fold activation of algD in PAO671 vs PAO381, under identical growth conditions (Table 6). Thus, inactivation of mucB is an event that results in increased algD transcription, alginate overproduction, and the establishment of mucoid phenotype.

TABLE 6

Effects of mucB inactivation on algD promoter activity

| Strain[a] | Phenotype[b] | algD::xylE activity[c] (U/mg of CDO) |
|---|---|---|
| PAO381 (mucB$^+$) | NM | 0.4 |
| PAO671 (mucB::$Tc^r$) | M | 10.5 |

[a]All strains harbored the algD::xylE transcription fusion plasmid pPAOM3 (Konyecsni and Deretic, 1989; Mohr et al., 1990).
[b]Phenotype was scored as mucoid (alginate producing) or nonmucoid after growth for 24 h on PIA.
[c]The activity was expressed as units of catechol 2,3 deoxygenase (CDO; the xylE gene product) per milligram of total protein in crude extracts. Standard error did not exceed 20%. Growth conditions, extract preparation, activity measurements, and unit definitions (see Experimental Procedures) are as previously described (Martin et al., 1992; Konyecsni and Deretic, 1989).

The experiments presented here demonstrate that inactivation of genes such as mucB can lead to a derepression of the algD promoter and conversion to mucoid (alginate overproducing) status. More importantly, using an isogenic series of strains, different frameshift mutations within the mucAB region that were present in several mucoid strains including CF isolates and absent in the nonmucoid strains have been detected, see Example 3.

A model founded on recently reported evidence (Martin et al., 1993), the results presented in this work, and studies by others (Fyfe and Govan, 1980; 1983; Costerton et al., 1983), is based on the premise that the synthesis of alginate and the emergence of alginate overproducing strains may be a developmental or a cell-differentiation process. Signal transduction involving response regulators such as AlgR and AlgB (Deretic et al., 1989; 1991; Wozniak and Ohman, 1991), nucleoid structure (Deretic et al., 1992; Mohr and Deretic, 1992), and activation of the specific sigma factor(s) (Martin et al., 1993) are most likely different contributing mechanisms for activation of alginate synthesis in natural environments. In the CF lung, while this environment may also be conducive to the induction of the alginate system, due to strong selective pressures (e.g. increased resistance of mucoid forms to phagocytosis, physical clearance mechanisms, antibiotic treatments, etc.) mutants are being selected that overproduce alginate and render cells constitutively mucoid. Such mutants, once extracted from the CF lung, retain mucoid character (Govan, 1988; Martin et al., unpublished results). Mutations in the algU-mucAB region, e.g. inactivation of mucA by frameshift mutations (see Example 3), or mutations affecting mucB activity, represent major pathways for conversion into the mucoid phenotype. Understanding of the principles of signal transduction processes activating the alginate system at several levels, as well as the precise definition of the mutations causing mucoidy in CF strains which is currently in progress, will provide improved diagnostic tools and present potential targets for therapeutic interventions.

EXAMPLE 3

Mechanism of Conversion to Mucoidy in *P. aeruginosa* Infecting Cystic Fibrosis Patients: Frameshift Mutations of mucA Cause Conversion to Mucoidy The references referred to in this example are listed at the end of the specification.

METHODS

In addition to those methods presented in Examples 1 and 2, the following methods were followed in the experiments described in this example.

Amplification of algU-mucA-mucB sequences, and hybridizations with allele specific oligonucleotides. The algU-mucA-mucB region was amplified using the following pairs of oligonucleotides: (i) UL5 GCCGCACGTCAC-GAGC and UR16 GAGTCCATCCGCTTCG for sequences containing mostly algU and a 5' portion of mucA; and (ii) UL3 CTGTCCGCTGTGATGG and UR12 CGCCCCT-GCTCCTCGA for sequences containing most of mucA and the entire mucB gene. For amplification of genomic sequences, a loopful of bacteria from a *P. aeruginosa* colony was washed in 0.85% saline, centrifuged, resuspended in 500 µl H$_2$O, boiled for 10 min, and stored at −20° until use. One µl of boiled preparations is sufficient to obtain necessary amounts of products for amplification by polymerase chain reaction (PCR). PCR was carried out in 50 µl volumes using standard procedures. Amplification products were tested by electrophoresis on agarose gels. Equal amounts of amplification products were electrophoretically separated on 1% agarose gels and then blotted onto a nitrocellulose filter using standard methods. After the transfer, and crosslinking using UV light (254 nm), blots were prehybridized in 10×SSC, 5×Denhardt solution (without BSA) for at least 30 min. Allele specific oligonucleotides were kinased with $^{32}$p following standard methods, purified using chromatography on Sep-Pak C$_{18}$ columns (Waters) and lyophilized by evaporation in a Savant SpeedVac apparatus. Hybridization with radiolabeled allele specific oligonucleotides was performed in 10 ml of 10×SSC, 5×Denhardt solution for 12 h at 42° C. Membranes were washed 3×for 10 min at 42° C. and autoradiograms taken overnight at −70° C. The blots were boiled for 3 min between hybridizations with different probes.

A simplified version of differential hybridization was also carried out using dot blots. In this case, 5 µl taken directly from the PCR mixture was blotted onto a nitrocellulose or nylon membrane presoaked in 10×SSC, and after denaturation, neutralization, crosslinking (by standard methods or as described above), hybridized and processed as explained for Southern blots.

RESULTS

Figure 11:
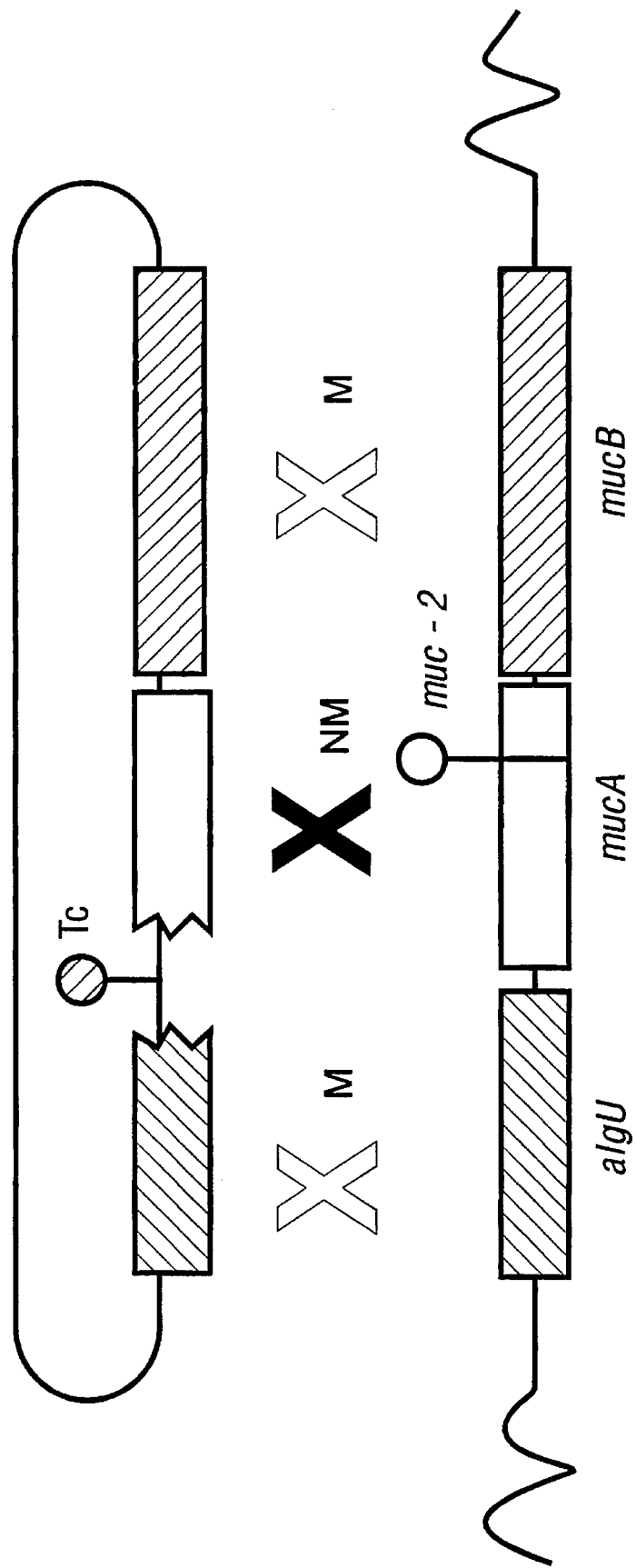
FIG. 11 shows the experimental design of a crossover between the chromosomal DNA of PAO568 and a plasmid containing a deletion that removed the 3' end of algU and the 5' end of the downstream gene mucA.
Figure 13:
FIG. 13 shows detection of muc mutations using allele-specific oligonucleotides as hybridization probes. The same Southern blot of PCR-amplified mucA-mucB regions from PAO381 (nonmucoid parental strain) and PAO568 (mucoid parental strain) was sequentially hybridized with two radiolabeled oligonucleotides: Oligo 381, specific for the wild type allele (mucA+); and oligo 568, specific for the mucA2 allele (see FIGS. 2A, 2B, 3A, and 3B). The hybridization was carried out at 42° C. in 10×SCC. Under these conditions the oligo 381 hybridizes to all alleles while the oligo 568 hybridizes only to the mucA2 allele.

In the course of performing gene replacements with algU in the mucoid strain PAO568 (carrying the muc-2 mutation), the present inventors discovered an informative class of recombinants. The gene replacements on the chromosome were carried out via homologous recombination with algU::Tc$^r$ on a plasmid that cannot replicate in Pseudomonas. A set of experiments was performed using a deletion that simultaneously removed the 3' end of algU and the 5' end of the downstream gene mucA (FIG. 11). Two types of recombinants were expected: (i) Nonmucoid strains containing true gene replacements with inactivated algU (results of double crossovers); and (ii) mucoid strains that were merodiploids (results of single crossovers). As expected, all double crossovers were nonmucoid since they lost a functional algU. The majority of merodiploids were mucoid, since they retained a functional copy of algU. However, a third class of recombinants was also observed which consisted of nonmucoid merodiploids. Since the plasmid DNA came from the nonmucoid strain PAO1, parental to the PAO568 lineage, a plausible explanation for the existence of nonmucoid merodiploids was that the crossover took place between the deletion in mucA on the plasmid and a putative mutation (muc- 2) in mucA on the chromosome of the mucoid strain PAO568. Only such a crossover could restore a wild type copy of mucA resulting in nonmucoid merodiploids (FIG. 11). The mutation had to be located between the EcoRV site of mucA, where the 5' deletion in the plasmid construct ended (FIG. 11), and the 3' end of mucA. In order to test this hypothesis, the present inventors cloned the corresponding region from the strain PAO568 by PCR and determined its complete nucleotide sequence in multiple independent clones. A duplication of 8 nucleotides at position 433 was observed within mucA in all PCR clones from PAO568 (FIG. 12A). The existence of this mutation was further confirmed by hybridization with allele specific oligonucleotides, oligo 381 and oligo 568 (see FIG. 12A and 12B), to PCR amplified chromosomal sequences from PAO568 (muc-2) and its direct nonmucoid parental strain PAO381 (FIG. 13). Next, the entire algU-mucAB region was cloned by PCR from PAO568 and its parental strain PAO381, and the complete nucleotide sequence of this region was determined in at least three independent clones. FIG. 14 contains the sequence of the mucA gene and encoded protein. The only difference between PAO381 (muc⁺) and PAO568 (muc-2) was the octanucleotide duplication in mucA. The present inventors concluded that this was the muc-2 mutation and the mucA allele was designated mucA2. The muc-2 mutation results in a frameshift causing premature termination of mucA at a downstream TGA codon (see FIG. 14).

Figures 15A, 15B:
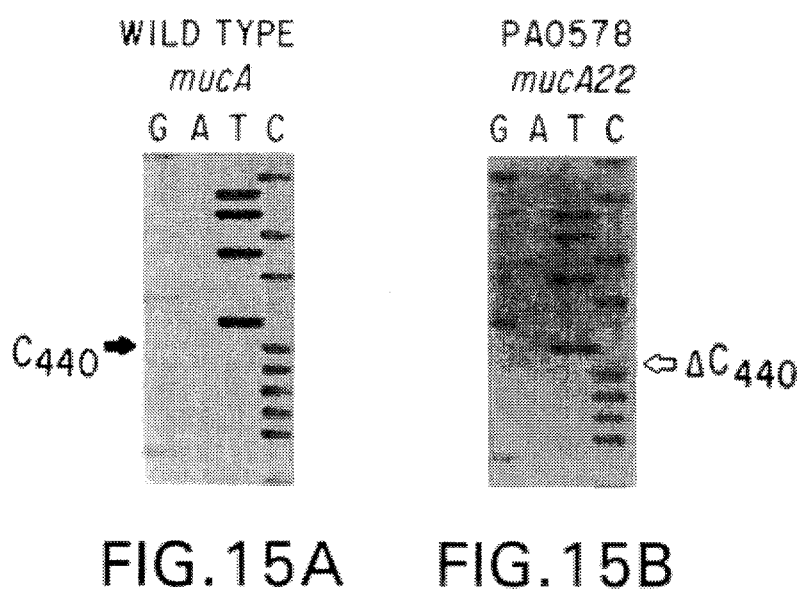
FIG. 15 shows a sequencing gel depicting the deletion of the "G" residue at position 439 or 440 (both are G residues) in PAO578. On the opposite DNA strand (which was sequenced) the deletion is a "C" residue.

The present inventors examined whether the allele specific oligonucleotides could be used to screen other mapped muc mutations in PAO and mucoid CF isolates. Although the oligonucleotide probe 568 (specific for the mucA2 allele) did not hybridize with the PCR amplified sequences from several strains, the control oligonucleotide (381) did hybridize but with a reduced intensity relative to PAO381. This suggested that although the tested strains did not have the octanucleotide duplication observed in mucA2, there were other alterations within the region complementary to the oligonucleotide probe. The corresponding regions from several strains hybridizing weakly with the oligonucleotide 381 were cloned and examined. The following strains were included: PAO578 (mucoid derivative of PAO381 with the mutation muc-22 mapping close to muc-2 as determined by transduction) and representative clinical mucoid isolates obtained from different cystic fibrosis patients. Following the procedure outlined for cloning and sequencing of the region encompassing the muc-2 mutation, the corresponding nucleotide sequences in the strain PAO578, and the clinical isolates tested were determined. Instead of the duplication of the octanucleotide sequence in PAO568, there was a deletion of a G residue within a string of 5 Gs within the same general region (see FIG. 15A and 15B). Since this was a deletion of one nucleotide, the net result was a similar frameshift as in PAO568, placing the same TGA termination codon in frame with the mucA sequence (see FIG. 14). The results of these analyses were additionally confirmed by designing an allele specific oligonucleotide designed for this mutation (oligo 578, see FIG. 12). The mutant allele in PAO578 was designated mucA22.

Figure 16:
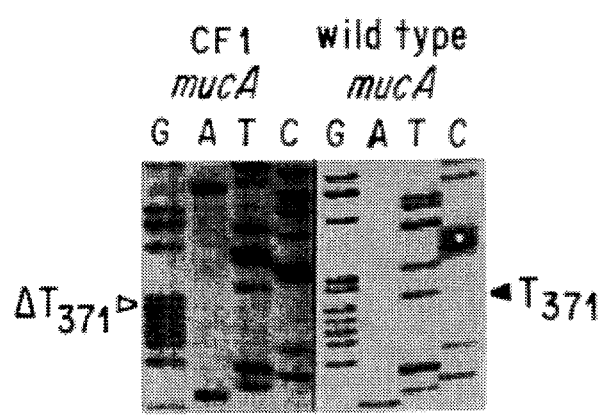
FIG. 16 shows a sequencing gel depicting the deletion of the "A" residue at position 371 in the CF1 isolate. On the opposite DNA strand (which was sequenced) the deletion is a "T" residue.

Next, the strains that were complemented by plasmids carrying the algU-mucAB region from PAO1 but did not show reduced hybridization with the oligonucleotides were examined. One such cystic fibrosis isolate was subjected to the same cloning and sequencing procedure as outlined above. No changes were detected within the location of the mucA2 and mucA22 mutations. Instead, a deletion of a single nucleotide at the position 371 was detected (see FIG. 16). This deletion was confirmed by sequencing multiple clones and by hybridizations with an allele specific oligonucleotide CF1 (see FIG. 12A and FIG. 12B). This frameshift mutation also results in a premature termination of mucA although at an upstream termination codon (see FIG. 14). Another strain, PAO581, that did not show differential hybridization with the allele specific oligonucleotides was also examined. PAO581 carries a muc mutation (muc-25) which has not be mapped by transduction. In this case the present inventors could not find any sequence differences between PAO581 and PAO381 within the region examined here. Similar to PAO581, several mucoid CF strains did not show detectable alterations in mucA.

The work described herein identifies a major site of mutations causing mucoidy in *P. aeruginosa*. The mucA gene and a tightly linked downstream gene, mucB are both required for suppression of mucoidy. When these functions are lost by insertional inactivation on the chromosome of previously nonmucoid strains, provided that the first gene of the cluster (algU) is intact, this results in a strong activation of algD transcription and conversion to mucoidy.

Mucoidy in *P. aeruginosa* has received attention mainly due to its association with CF. However, almost all strains of *P. aeruginosa* have the genetic capacity to synthesize alginate suggesting that this system must play a role in other ecological niches. The vast majority of *P. aeruginosa* biomass in nature exists as the form embedded in the exopolysaccharide biofilm attached to surfaces. It has been shown that *P. aeruginosa* undergoes interconversions between the free floating planktonic form and the sessile form in biofilms, a process which has been viewed as a developmental or cell differentiation phenomenon. Regulation of alginate production by a factor (algU) homologous to an alternative sigma factor SpoOH, controlling the initial stages of development in Bacillus spp. (e.g. sporulation and competence), may reflect the nature of regulatory processes controlling development of biofilms. The genetic data indicate that mucA and mucB suppress the function of algU. There are now ample examples of accessory factors associated with or linked to alternative sigma factors in Bacillus and other organisms that post-translationally modify (e.g. inhibit) their function. By analogy, MucA and MucB may play a similar role. This system, along with signal transduction regulators and histone-like elements, is likely designed to control development of biofilms in response to appropriate environmental cues. Mutations in mucA that lock the system in its constitutive state, which is favorable due to the antiphagocytic properties of the mucoid coating, are being selected in the course of chronic respiratory infection in CF.

In addition to the improved understanding of the molecular mechanisms controlling an important bacterial virulence factor, several aspects of the regulation of mucoidy presented here shed light on developmental processes in Gram negative organisms. The finding that algU shows similarities with a sigma factor specializing in developmental processes of a Gram positive sporulating organism, suggests that bacterial cell differentiation phenomena (e.g. sporulation, biofilm development, and bacterial encystment) may share common regulatory mechanisms.

The following references are specifically incorporated by reference herein in pertinent part.

REFERENCES

Ausubel, F. M., Brent, R., Kingston, R. E., Moore, D. D., Seidman, J. G., Smith, J. A., and Struhl, K. (1989) Current protocols in molecular biology. John Wiley & Sons, Inc., New York.

Berry, A., DeVault, J. D., and Chakrabarty, A.M. (1989) High osmolarity is a signal for enhanced algD transcription in mucoid and nonmucoid *Pseudomonas aeruginosa* strains. J. Bacteriol. 171:2312–2317.

Burbulys, D., Trach, K. A., and Hoch, J.A. (1991) Initiation of sporulation in *B. subtilis* is controlled by a multicomponent phosphorelay. Cell 64:545–552.

Chitnis et al., 1990, "Cloning of *Pseudomonas aeruginosa* algG, which controls alginate structure" *J. Bacteriol* 172(6): 2894–2900.

Costerton, J. W., Cheng, K.-J., Geesey, G. G., Ladd, T. I., Nickel, J. C., Dasgupta, M., Marrie, T. J. (1987) Bacterial biofilms in nature and disease. Ann. Rev. Microbiol. 41:435–464.

Costerton, J. W., Lam, J., Lam, K., and Chan, R. (1983) The role of the microcolony mode of growth in the pathogenesis of *Pseudomonas aeruginosa* infections. Rev. Infect. Dis. 5:S867–S873.

Darzins, A., Wang, S. K., Vanags, R. I., and Chakrabarty, A. M. (1985) Clustering of mutations affecting alginic acid biosynthesis in mucoid *Pseudomonas aeruginosa.* J. Bacteriol. 164:516–524.

DeVault, J. D., Kimbara, K., and Chakrabarty, A. M. (1990) Pulmonary dehydration and infection in cystic fibrosis: evidence that ethanol activates alginate gene expression and induction of mucoidy in *Pseudomonas aeruginosa.* Mol. Microbiol. 4:737–745.

Deretic, V., Gill, J. F., and Chakrabarty, A.M. (1987) Gene algD coding for GDPmannose dehydrogenase is transcriptionally activated in mucoid *Pseudomonas aeruginosa.* J. Bacteriol. 169:351–358.

Deretic, V., Konyecsni, W. M., Mohr, C. D., Martin, D. W., and Hibler, N. S. (1989) Common denominators of promoter control in Pseudomonas and other bacteria. Bio/Technology 7:1249–1254.

Deretic, V., Dikshit, R., Konyecsni, W. M., Chakrabarty, A. M., and Misra, T. K. (1989) The algR gene, which regulates mucoidy in *Pseudomonas aeruginosa,* belongs to a class of environmentally responsive genes. J. Bacteriol. 171:1278–1283.

Deretic, V., Govan, J. R. W., Konyecsni, W. M., and Martin, D. W. (1990) Mucoid Pseudomonas aeruginosa in cystic fibrosis: mutations in the muc loci affect transcription of the algR and algD genes in response to environmental stimuli. Mol. Microbiol. 4:189–196.

Deretic, V., Mohr, C. D., and Martin, D. W. (1991) Mucoid *Pseudomonas aeruginosa* in cystic fibrosis: signal transduction and histone-like elements in the regulation of bacterial virulence. Mol. Microbiol. 5:1557–1583.

Deretic, V., Hibler, N. S. and Holt, S.C. (1992) Immunocytochemical analysis of AlgP ($H_p1$), a histonelike element participating in control of mucoidy in *Pseudomonas aeruginosa.* J. Bacteriol. 174:824–831.

Dubnau, D. (1991) The regulation of genetic competence in *Bacillus subtilis.* Mol. Microbiol. 5:11–18.

Dubnau, E., Weir, J., Nair, G., Carter III, L., Moran, Jr., C., and Smith, I. (1988) Bacillus sporulation gene spo0H codes for $^{30}$ ($^4$). J. Bacteriol. 170:1054–1062.

Flynn, J. L., and Ohman, D. E. (1988) Cloning of genes from mucoid *Pseudomonas aeruginosa* which control spontaneous conversion to the alginate production phentotype. J. Bacteriol. 170:1452–1460.

Flynn, J. L., and Ohman, D. E. (1988b) Use of gene replacement cosmid vector for cloning alginate conversion genes from mucoid and nonmucoid *Pseudomonas aeruginosa* strains: algS controls expression of algT. J. Bacteriol. 170:3228–3236.

Fyfe, J. A. M., and Govan, J. R. W. (1980) Alginate synthesis in mucoid *Pseudomonas aeruginosa:* a chromosomal locus involved in control. J. Gen. Microbiol. 119:443–450.

Fyfe, J. A. M., and Govan, J. R. W. (1983) Synthesis, regulation and biological function of bacterial alginate. In Progress in inductrial microbiology, vol. 18 (Bushell, M. E., ed.). Elsevier, Amsterdam, pp. 45–83.

Goldberg et al., 1992, "Pseudomonas aeruginosa algB which modulates the expression of alginate, is a member of the NTrC subclass of prokaryotic regulators", Mol Microbiol 6(1): 59–66

Govan, J. R. W. (1988) Alginate biosynthesis and other unusual characteristics associated with the pathogenesis of *Pseudomonas aeruginosa* in cystic fibrosis. p. 67–96. In E. Griffiths, W. Donachie, and J. Stephen, (eds.), Bacterial infections of respiratory and gastrointestinal mucosae. IRL Press, Oxford.

Govan et al. 1992, "Mucoid *Pseudomonas aeruginosa* and cystic fibrosis: The role of mutations in muc loci" FEMS MICROBIOL. LETT. 100(1–3): 323–329.

Kalman, S., Duncan, M. L., Thomas, S. M., and Price, C. W. (1990) Similar organization of the sigB and spoIIA operons encoding alternate sigma factors of *Bacillus subtilis* RNA polymerase. J. Bacteriol. 172:5575–5585.

Knutson, C. A., and Jeanes, A. (1976) A new modification of the carbazole reaction: application to heteropolysaccharides. Anal. Biochem. 24:470–481.

Konyecsni, W. M., and Deretic, V. (1989) Broad-host-range plasmid and M13 bacteriophage-derived vectors for promoter analysis in *Escherichia coli* and *Pseudomonas aeruginosa.* Gene 74:375–386.

Konyecsni et al., 1990, "DNA Sequence and Expression analysis of algP and algQ, components of the multigene system transcriptionally regulating mucoidy in *Pseudomonas aeruginosa:* algP contains multiple direct repeats", J. Bacteriol 172(5):2511–2520.

Losick, R., Youngman, P., and Piggot, P. J. (1986) Genetics of endospore formation in *Bacillus subtilis.* Ann. Rev. Genet. 20:625–669.

Martin, D. W., Holloway, B. W., and Deretic, V. (1993) Characterization of a locus determining the mucoid status of *Pseudomonas aeruginosa:* algU shows sequence similarities with a Bacillus sigma factor. J. Bacteriol. 175:000–000.

May, T. B., Shinaberger, D., Maharaj, R., Kato, J., Chu, L., DeVault, J. D., Roychoudhury, S., Zieleinski, N. A., Berry, A., Rothmel, R. K., Misra, T. K., and Chakrabarty, A. M. (1991) Alginate synthesis by *Pseudomonas aeruginosa:* a key pathogenic factor in chronic pulmonary infections in cystic fibrosis. Clin. Microbiol. Rev. 4:191–206.

Mohr, C. D., Martin, D. W., Konyecsni, W. M., Govan, J. R. W., Lory, S., and Deretic, V. (1990) Role of the far-upstream sites of the algD promoter and the algR and rpoN genes in environmental modulation of mucoidy in *Pseudomonas aeruginosa.* J. Bacteriol. 172:6576–6580.

Mohr, C. D. M., Hibler, N. S., and Deretic, V. (1991) AlgR, a response regulator controlling mucoidy in *Pseudomonas aeruginosa,* binds to the FUS sites of the algD promoter located unusually far upstream from the mRNA start site. J. Bacteriol. 173:5136–5143.

Mohr, C. D., Leveau, J. H. J., Krieg, D. P., Hibler, N. S., and Deretic, V. (1992) AlgR-binding sites within the algD promoter make up a set of inverted repeats separated by a large intervening segment of DNA. J. Bacteriol. 174:6624–6633.

Mohr, C. D., and Deretic, V. (1992) In vitro interactions of the histone-like protein IHF with the algD promoter, a critical site for control of mucoidy in *Pseudomonas aeruginosa.* Biochem. Biophys. Res. Com. 189:837–844.

Ohman, D. E., Goldberg, J. B., and Flynn, J. L. (1990) Molecular analysis of the genetic switch activating alginate production. In: S. Silver, A.M. Chakrabarty, B. Iglewski, and S. Kaplan (eds.), Pseudomonas biotransformations, pathogenesis, and evolving biotechnology. American Society for Microbiology, Washington, D.C.

Ohnishi, K., Kutsukake, K., Suzuki, H., and Ino, T. (1992) A novel transcriptional regulation mechanism in the flagellar regulon of Salmonella typhimurium: an anti-sigma factor inhibits the activity of the flagellum-specific sigma factor, $\_^F$. Mol. Microbiol. 6:3149–3157.

Pedersen, S.S., Kharazmi, A., Espersen, F., and Hoiby, N. (1990) *Pseudomonas aeruginosa* alginate in cystic fibrosis sputum and the inflammatory response. Infect. Immun. 58:3363–3368.

Pier, G. B. (1992) Role of opsonic antibodies in defense against *Pseudomonas aeruginosa* in cystic fibrosis. Pediatric Pulm. S8:163–164.

Pier, G. B., Saunders, J. M., and Ames, P. (1987) Opsonophagocytic killing antibody to *Pseudomonas aeruginosa* mucoid exopolysaccharide in older, non-colonized cystic fibrosis patients. N. Engl. J. Med. 317:793–798.

Pier, G. B., Small, G. J., and Warren, H. B. (1990) Protection against mucoid *Pseudomonas aeruginosa* in rodent models of endobronchial infections. Science 249:537–540.

Presslet, T., Pandey, J. P., Espersen, F., Pedersen, S. S., Fomsgaard, A., Koch, C., and Hoiby, N. (1992) Immunoglobulin allotypes and IgG subclass antibody response to *Pseudomonas aeruginosa* antigens in chronically infected cystic fibrosis patients. Clin. Exp. Immunol. 90:209–214.

Sadoff, H. L. (1975) Encystment and germination in Azotobacter vinelandii. Bacteriol. Rev. 39:516–539.

Schmidt, R., Margolis, P., Duncan, L., Coppolecchia, R., Moran, C. P., Jr., and Losick, R. (1990) Control of developmental transcription factor $\_^F$ by sporulation regulatory proteins SpoIIAA and SpoIIAB in *Bacillus subtilis*. Proc. Natl. Acad. Sci. USA 87:9221–9225.

Selvaraj, C., Fong, Y. C., and Iyer, V. N. (1984) A portable DNA sequence carrying the cohesive site (cos) of bacteriophage and the mob (mobilization) region of the broad-host-range plasmid RK2: a module for the construction of new cosmids. Gene 32:235–241.

Stragier, P., Kunkel, B., Kroos, L., and Losick, R. (1989) Chromosomal rearrangements generating a composite gene for a developmental transcription factor. Science 243:507–512.

Tabor, S., and Richardson, C. C. (1985) A bacteriophage T7 RNA polymerase/promoter system for controlled expression of specific genes. Proc. Natl. Acad. Sci. USA 82:1074–1078.

Terry, J. M., Pina, S. E., and Mattingly, S.J. (1991) Environmental conditions which influence mucoid conversion in *Pseudomonas aeruginosa* PAO1. Infect. Immun. 59:471–477.

Tosi, M. F., Zakem, H., and Berger, M. (1990) Neutrophil elastase cleaves C3bi on opsonized Pseudomonas as well as CR1 on neutrophils to create a functionally important opsonin receptor mismatch. J. Clin. Invest. 86:300–308.

Totten, P. A., Lara, J. C., and Lory, S. (1990) The rpoN gene product of *Pseudomonas aeruginosa* is required for expression of diverse genes, including the flagellin gene. J. Bacteriol. 172:389–396.

Trempy, J. E., Morrison-Plummer, J., and Haldenwang, W. G. (1985) Synthesis of $\_^{29}$, and RNA polymerase specificity determinant, is a developmentally regulated event in *Bacillus subtilis*. J. Bacteriol. 161:340–346.

West, S. E., and Iglewski, B. H. (1988) Codon usage in *Pseudomonas aeruginosa*. Nucleic Acids Res. 16:9323–9335.

Wozniak, D. J., and Ohman, D. E. (1991) *Pseudomonas aeruginosa* AlgB, a two-component response regulator of the NtrC family, is required for algD transcription. J. Bacteriol. 173:1406–1413.

Zielinski et al., 1992, "Alginate Synthesis in *Pseudomonas aeruginosa*: environmental regulation of the algC promoter", J. Bacteriol. 174(23):7680–7688.

---

What is claimed is:

1. A first polynucleotide having the sequence of SEQ ID NO. 10, a second polynucleotide complementary to the first polynucleotide, or a third polynucleotide differing from the first or second polynucleotide by codon degeneracy, wherein the first, second, and third polynucleotides are purified from total genomic Pseudomonas DNA.

2. A *Pseudomonas aeruginosa* mucA gene in substantially pure form defined as having the sequence of SEQ ID NO. 1.

3. The mucA gene of claim 2 defined further as having a frameshift mutation at position 371, 433, 439 or 440.

4. A mucA gene of claim 3 wherein the frameshift mutation is an insertion of eight nucleotides at position 433 or a deletion of one nucleotide from position 371, 439, or 440.

5. The mucA gene of claim 3 wherein the frameshift mutation results in premature termination of translation of a mucA gene product.

6. The mucA gene of claim 3 wherein the frameshift mutation is the deletion of nucleotide "A" from position 371.

7. The mucA gene of claim 3 wherein the frameshift mutation is the deletion of nucleotide "G" from position 439 or 440.

8. The mucA gene of claim 3 wherein the frameshift mutation is the insertion of 5'-CAGGGGGC-3' at position 433.

9. A first polynucleotide having the sequence of SEQ ID NO. 1, a second polynucleotide complementary to the first polynucleotide or a third polynucleotide differing from the first or second polynucleotide by codon degeneracy, wherein the first, second, and third polynucleotides are purified from total genomic Pseudomonas DNA.

* * * * *

UNITED STATES PATENT AND TRADEMARK OFFICE
CERTIFICATE OF CORRECTION

PATENT NO. : 5,591,838

DATED : January 7, 1997

INVENTOR(S) : Vojo Deretic and Daniel W. Martin

It is certified that error appears in the above-identified patent and that said Letters Patent is hereby corrected as shown below:

In claim 1, column 47, line 41, delete ",".

Signed and Sealed this

Twenty-second Day of April, 1997

Attest:

BRUCE LEHMAN

*Commissioner of Patents and Trademarks*

*Attesting Officer*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 595 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AGGTATCGCT  ATGAGTCGTG  AAGCCCTGCA  GGAAACTCTG  TCCGCTGTGA  TGGATAACGA    60
AGCGGATGAA  CTCGAGTTGC  GGCGGGTGCT  CGCAGCTTGC  GGCGAGGATG  CCGAGCTGCG   120
TTCCACCTGG  TCGCGTTACC  AGTTGGCGCG  GTCCGTCATG  CACCGCGAGC  CTACCCTGCC   180
GAAGCTGGAT  ATCGCTGCGG  CGGTCTCTGC  TGCCCTGGCC  GACGAGGCCG  CTCCGCCGAA   240
AGCGGAGAAG  GGACCGTGGC  GGATGGTCGG  TCGCCTGGCG  GTCGCTGCCT  CGGTGACCCT   300
GGCGGTGCTG  GCCGGCGTGC  GTCTGTACAA  CCAGAACGAC  GCCCTGCCGC  AAATGGCGCA   360
ACAGGGGACC  ACCCCGCAGA  TCGCCCTGCC  TCAGGTGAAA  GGCCCGGCCG  TGCTGGCCGG   420
```

| CTACAGCGAA | GAGCAGGGGG | CGCCGCAGGT | GATCACCAAC | TCCTCGTCCA | GCGATACCCG | 480 |
| CTGGCATGAG | CAGCGTCTGC | CGATCTACCT | GCGTCAGCAC | GTGCAACAAT | CCGCCGTCAG | 540 |
| TGGTACAGAG | AGCGCGCTGC | CCTACGCTCG | GGCAGCCAGC | CTGGAAAACC | GCTGA | 595 |

( 2 ) INFORMATION FOR SEQ ID NO:2:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

GGGACCCCCC GCA                                                        13

( 2 ) INFORMATION FOR SEQ ID NO:3:

( i ) SEQUENCE CHARACTERISTICS:
        ( A ) LENGTH: 13 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:3:

GAGCAGGGGC GCC                                                        13

( 2 ) INFORMATION FOR SEQ ID NO:4:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:4:

CAGGGGGCCA GGGGGC                                               16

( 2 ) INFORMATION FOR SEQ ID NO:5:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:5:

GCCGCACGTC ACGAGC                                               16

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:6:

GAGTCCATCC GCTTCG                                                                                                      16

(2) INFORMATION FOR SEQ ID NO:7:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:7:

CTGTCCGCTG TGATGG                                                                                                      16

(2) INFORMATION FOR SEQ ID NO:8:

(i) SEQUENCE CHARACTERISTICS:
      (A) LENGTH: 16 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:8:

CGCCCCTGCT CCTCGA                                                                                                      16

(2) INFORMATION FOR SEQ ID NO:9:

(i) SEQUENCE CHARACTERISTICS:
      (A) LENGTH: 647 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:9:

GTCTATCTTG GCAAGACGAT TCGCTGGGAC GCTCGAAGCT CCTCCAGGTT CGAAGAGGAG       60
CTTTCATGCT AACCCAGGAA CAGGATCAGC AACTGGTTGA ACGGGTACAG CGCGGAGACA      120
AGCGGGCTTT CGATCTGCTG GTACTGAAAT ACCAGCACAA GATACTGGGA TTGATCGTGC      180
GGTTCGTGCA CGACGCCCAG GAAGCCCAGG ACGTAGCGCA GGAAGCCTTC ATCAAGGCAT      240
ACCGTGCGCT CGGCAATTTC CGCGGCGATA GTGCTTTTTA TACCTGGCTG TATCGGATCG      300
CCATCAACAC CGCGAAGAAC CACCTGGTCG CTCGCGGGCG TCGGCCACCG GACAGCGATG      360
TGACCGCAGA GGATGCGGAG TTCTTCGAGG GCGACCACGC CCTGAAGGAC ATCGAGTCGC      420
CGGAACGGGC GATGTTGCGG GATGAGATCG AGGCCACCGT GCACCAGACC ATCCAGCAGT      480
TGCCCGAGGA TTTGCGCACG GCCCTGACCC TGCGCGAGTT CGAAGGTTTG AGTTACGAAG      540
ATATCGCCAC CGTGATGCAG TGTCCGGTGG GGACGGTACG GTCGCGGATC TTCCGCGCTC      600
GTGAAGCAAT CGACAAAGCT CTGCAGCCTT TGTTGCGAGA AGCCTGA                    647

(2) INFORMATION FOR SEQ ID NO:10:

(i) SEQUENCE CHARACTERISTICS:
      (A) LENGTH: 1800 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:10:

| | | | | | | |
|---|---|---|---|---|---|---|
| TTTGTTGCGA | GAAGCCTGAC | ACAGCGGCAA | ATGCCAAGAG | AGGTATCGCT | ATGAGTCGTG | 60 |
| AAGCCCTGCA | GGAAACTCTG | TCCGCTGTGA | TGGATAACGA | AGCGGATGAA | CTCGAGTTGC | 120 |
| GGCGGGTGCT | CGCAGCTTGC | GGCGAGGATG | CCGAGCTGCG | TTCCACCTGG | TCGCGTTACC | 180 |
| AGTTGGCGCG | GTCCGTCATG | CACCGCGAGC | CTACCCTGCC | GAAGCTGGAT | ATCGCTGCGG | 240 |
| CGGTCTCTGC | TGCCCTGGCC | GACGAGGCCG | CTCCGCCGAA | AGCGGAGAAG | GGACCGTGGG | 300 |
| GGATGGTCGG | TCGCCTGGCG | GTCGCTGCTC | GGTGACCCTG | GCGGTGCTGG | CCGGCGTGCG | 360 |
| TCTGTACAAC | CAGAACGACG | CCCTGCCGCA | AATGGCGCAA | CAGGGGACCA | CCCCGCAGAT | 420 |
| CGCCCTGCCT | CAGGTGAAAG | GCCCGGCCGT | GCTGGCCGGC | TACAGCGAAG | AGCAGGGGGC | 480 |
| GCCGCAGGTG | ATCACCAACT | CCTCGTCCAG | CGATACCCGC | TGGCATGAGC | AGCGTCTGCC | 540 |
| CGATCTACCT | GCGTCAGCAC | GTGCAACAAT | CCGCCGTCAG | TGGTACAGAG | AGCGCGCTGC | 600 |
| CCTACGCTCG | GGCAGCCAGC | CTGGAAAACC | GCTGAGGAGA | GACATGCGCA | CCACCTCCCT | 660 |
| GTTGCTTTTG | CTTGGCAGCC | TGATGGCGGT | TCCCGCCACT | CAGGCTGCCG | ACGCTTCCGA | 720 |
| CTGGCTGAAT | CGTCTCGCCG | AGGCCGATCG | CCAGAACAGT | TTCCAAGGCA | CCTTCGTCTA | 780 |
| CGAGCGCAAT | GGCAGCTTCT | CCACCCATGA | GATCTGGCAT | CGCGTGGAGA | GCGATGGTGC | 840 |
| GGTTCGCGAG | CGCCTGCTCC | AGCTCGACGG | CGCGCGCCAG | GAAGTGGTCC | GGGTCGACGG | 900 |
| GCGCACCCAG | TGCATCAGCG | GCGGCCTTGC | CGACCAACTG | GCCGATGCCC | AGCTGTGGCC | 960 |
| GGTGCGCAAG | TTCGATCCCT | CCCAGCTGGC | TTCCTGGTAC | GACCTGCGCC | TGGTCGGGGA | 1020 |
| ATCCCGTGTC | GCCGGCCGCC | CGGCAGTGGT | CCTTGCGGTG | ACTCCGCGCG | ACCAGCATCG | 1080 |
| CTACGGCTTC | GAGCTGCACC | TGGACCGCGA | CACCGGCCTG | CCGTTGAAGT | CGCTGCTGCT | 1140 |
| GAACGAGAAG | GGGCAGTTGC | TCGAGCGCTT | CCAGTTCACC | CAGTTGAATA | CCGGCGCGGC | 1200 |
| ACCTGCCGAA | GACCAGTTGC | AGGCGGGCGC | CGAATGCCAG | GTCGTCGGCC | CGGCCAAGGC | 1260 |
| CGACGGGGAG | AAGACCGTGG | CCTGGCGCTC | GGAATGGCTG | CCGCCAGGTT | TCACCCTGAC | 1320 |
| CCGCAGTTTC | ATGCGTCGCA | GTCCGGTCAC | CCCCGATCCG | GTCGCCTGCC | TGACCTATGG | 1380 |
| CGATGGCCTG | GCACGATTCT | CGGTGTTCAT | CGAGCCGCTG | CACGGTGCCA | TGGTTGGCGA | 1440 |
| CGCGCGCAGC | CAGCTCGGCC | CGACCGTGGT | GGTTTCCAAG | CGCCTGCAGA | CCGATGACGG | 1500 |
| CGGCCAGATG | GTGACCGTCG | TCGGCGAAGT | GCCGCTGGGC | ACCGCCGAGC | GGGTGGCGCT | 1560 |
| GTCCATCCGG | CCCGAGGCCG | CCGCCCAGAA | ATGATCGAGG | AGCAGGGGCG | AGTGGTGGCG | 1620 |
| ACCGAGCCGG | GAGCGGTATG | GGTCGAGACC | GTGCGCCGAG | TACCTGCTCG | TCCTGCTCGG | 1680 |
| CCAATGCCGG | TTGCGGCCAG | GGCTGATGC | AGCGCCTGGG | CGTCGGCGCG | GGGCGTGCCC | 1740 |
| GGGTGCGCGC | GTTGAGCGAC | CTGAGCCTGC | GGGTCGGCGA | TGCGGTCGTC | CTAGGAATTC | 1800 |

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:11:

AGCGAAGAGC AGGGGCGCC GCAGGTGATC A        31

(2) INFORMATION FOR SEQ ID NO:12:

(i) SEQUENCE CHARACTERISTICS:
        (A) LENGTH: 15 base pairs (B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:12:

GAGCAGGGGG CGCCG     15

(2) INFORMATION FOR SEQ ID NO:13:

(i) SEQUENCE CHARACTERISTICS:
(A) LENGTH: 26 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:13:

AACAGGGGAC CACCCCGCAG ATCGCC     26

(2) INFORMATION FOR SEQ ID NO:14:

(i) SEQUENCE CHARACTERISTICS:
(A) LENGTH: 13 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:14:

GGGACCACCC CGC     13

(2) INFORMATION FOR SEQ ID NO:15:

(i) SEQUENCE CHARACTERISTICS:
(A) LENGTH: 194 amino acids
(B) TYPE: amino acid
(C) STRANDEDNESS: single
(D) TOPOLOGY: linear (ii) MOLECULE TYPE: peptide (xi) SEQUENCE DESCRIPTION: SEQ ID NO:15:

```
Met Ser Arg Glu Ala Leu Gln Glu Thr Leu Ser Ala Val Met Asp Asn
 1               5                  10                  15

Glu Ala Asp Glu Leu Glu Leu Arg Arg Val Leu Ala Ala Cys Gly Glu
            20                  25                  30

Asp Ala Glu Leu Arg Ser Thr Trp Ser Arg Tyr Gln Leu Ala Arg Ser
            35                  40                  45

Val Met His Arg Glu Pro Thr Leu Pro Lys Leu Asp Ile Ala Ala Ala
    50                  55                  60

Val Ser Ala Ala Leu Ala Asp Glu Ala Ala Pro Pro Lys Ala Glu Lys
65                  70                  75                  80

Gly Pro Trp Arg Met Val Gly Arg Leu Ala Val Ala Ala Ser Val Thr
                85                  90                  95

Leu Ala Val Leu Ala Gly Val Arg Leu Tyr Asn Gln Asn Asp Ala Leu
                100                 105                 110

Pro Gln Met Ala Gln Gln Gly Thr Thr Pro Gln Ile Ala Leu Pro Gln
            115                 120                 125

Val Lys Gly Pro Ala Val Leu Ala Gly Tyr Ser Glu Gln Gly Ala
            130                 135                 140
```

```
Pro Gln Val Ile Thr Asn Ser Ser Ser Asp Thr Arg Trp His Glu
145                 150             155                 160

Gln Arg Leu Pro Ile Tyr Leu Arg Gln His Val Gln Gln Ser Ala Val
                165             170                 175

Ser Gly Thr Glu Ser Ala Leu Pro Tyr Ala Arg Ala Ala Ser Leu Glu
            180             185                 190

Asn Arg
```

( 2 ) INFORMATION FOR SEQ ID NO:16:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:16:

```
Leu Leu Arg Glu Ala
1               5
```

( 2 ) INFORMATION FOR SEQ ID NO:17:

( i ) SEQUENCE CHARACTERISTICS:
        ( A ) LENGTH: 194 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:17:

```
Met Ser Arg Glu Ala Leu Gln Glu Thr Leu Ser Ala Val Met Asp Asn
1               5                   10                  15

Glu Ala Asp Glu Leu Glu Leu Arg Arg Val Leu Ala Ala Cys Gly Glu
            20                  25                  30

Asp Ala Glu Leu Arg Ser Thr Trp Ser Arg Tyr Gln Leu Ala Arg Ser
        35                  40                  45

Val Met His Arg Glu Pro Thr Leu Pro Lys Leu Asp Ile Ala Ala Ala
50                  55                  60

Val Ser Ala Ala Leu Ala Asp Glu Ala Ala Pro Pro Lys Ala Glu Lys
65                  70                  75                  80

Gly Pro Trp Arg Met Val Gly Arg Leu Ala Val Ala Ala Ser Val Thr
                85                  90                  95

Leu Ala Val Leu Ala Gly Val Arg Leu Tyr Asn Gln Asn Asp Ala Leu
                100             105                 110

Pro Gln Met Ala Gln Gln Gly Thr Thr Pro Gln Ile Ala Leu Pro Gln
            115             120                 125

Val Lys Gly Pro Ala Val Leu Ala Gly Tyr Ser Glu Gln Gly Ala
    130             135                 140

Pro Gln Val Ile Thr Asn Ser Ser Ser Asp Thr Arg Trp His Glu
145                 150             155                 160

Gln Arg Leu Pro Ile Tyr Leu Arg Gln His Val Gln Gln Ser Ala Val
                165             170                 175

Ser Gly Thr Glu Ser Ala Leu Pro Tyr Ala Arg Ala Ala Ser Leu Glu
            180             185                 190

Asn Arg
```

( 2 ) INFORMATION FOR SEQ ID NO:18:

( i ) SEQUENCE CHARACTERISTICS:
   ( A ) LENGTH: 316 amino acids
   ( B ) TYPE: amino acid
   ( C ) STRANDEDNESS: single
   ( D ) TOPOLOGY: linear ( i i ) MOLECULE TYPE: peptide ( x i ) SEQUENCE DESCRIPTION: SEQ ID NO:18:

| Met | Arg | Thr | Thr | Ser | Leu | Leu | Leu | Leu | Leu | Gly | Ser | Leu | Met | Ala | Val |
|---|---|---|---|---|---|---|---|---|---|---|---|---|---|---|---|
| 1 | | | | 5 | | | | | 10 | | | | | 15 | |

| Pro | Ala | Thr | Gln | Ala | Ala | Asp | Ala | Ser | Asp | Trp | Leu | Asn | Arg | Leu | Ala |
| | | | 20 | | | | | 25 | | | | | 30 | | |

| Glu | Ala | Asp | Arg | Gln | Asn | Ser | Phe | Gln | Gly | Thr | Phe | Val | Tyr | Glu | Arg |
| | | | 35 | | | | | 40 | | | | | 45 | | |

| Asn | Gly | Ser | Phe | Ser | Thr | His | Glu | Ile | Trp | His | Arg | Val | Glu | Ser | Asp |
| | | 50 | | | | | 55 | | | | | 60 | | | |

| Gly | Ala | Val | Arg | Glu | Arg | Leu | Leu | Gln | Leu | Asp | Gly | Ala | Arg | Gln | Glu |
| 65 | | | | | 70 | | | | | 75 | | | | | 80 |

| Val | Val | Arg | Val | Asp | Gly | Arg | Thr | Gln | Cys | Ile | Ser | Gly | Gly | Leu | Ala |
| | | | | 85 | | | | | 90 | | | | | 95 | |

| Asp | Gln | Leu | Ala | Asp | Ala | Gln | Leu | Trp | Pro | Val | Arg | Lys | Phe | Asp | Pro |
| | | | 100 | | | | | 105 | | | | | 110 | | |

| Ser | Gln | Leu | Ala | Ser | Trp | Tyr | Asp | Leu | Arg | Leu | Val | Gly | Glu | Ser | Arg |
| | | | 115 | | | | | 120 | | | | | 125 | | |

| Val | Ala | Gly | Arg | Pro | Ala | Val | Val | Leu | Ala | Val | Thr | Pro | Arg | Asp | Gln |
| | | | 130 | | | | | 135 | | | | | 140 | | |

| His | Arg | Tyr | Gly | Phe | Glu | Leu | His | Leu | Asp | Arg | Asp | Thr | Gly | Leu | Pro |
| 145 | | | | | 150 | | | | | 155 | | | | | 160 |

| Leu | Lys | Ser | Leu | Leu | Leu | Asn | Glu | Lys | Gly | Gln | Leu | Leu | Glu | Arg | Phe |
| | | | | 165 | | | | | 170 | | | | | 175 | |

| Gln | Phe | Thr | Gln | Leu | Asn | Thr | Gly | Ala | Ala | Pro | Ala | Glu | Asp | Gln | Leu |
| | | | 180 | | | | | 185 | | | | | 190 | | |

| Gln | Ala | Gly | Ala | Glu | Cys | Gln | Val | Val | Gly | Pro | Ala | Lys | Ala | Asp | Gly |
| | | 195 | | | | | 200 | | | | | 205 | | | |

| Glu | Lys | Thr | Val | Ala | Trp | Arg | Ser | Glu | Trp | Leu | Pro | Pro | Gly | Phe | Thr |
| | 210 | | | | | 215 | | | | | 220 | | | | |

| Leu | Thr | Arg | Ser | Phe | Met | Arg | Arg | Ser | Pro | Val | Thr | Pro | Asp | Pro | Val |
| 225 | | | | | 230 | | | | | 235 | | | | | 240 |

| Ala | Cys | Leu | Thr | Tyr | Gly | Asp | Gly | Leu | Ala | Arg | Phe | Ser | Val | Phe | Ile |
| | | | | 245 | | | | | 250 | | | | | 255 | |

| Glu | Pro | Leu | His | Gly | Ala | Met | Val | Gly | Asp | Ala | Arg | Ser | Gln | Leu | Gly |
| | | | 260 | | | | | 265 | | | | | 270 | | |

| Pro | Thr | Val | Val | Val | Ser | Lys | Arg | Leu | Gln | Thr | Asp | Asp | Gly | Gly | Gln |
| | | 275 | | | | | 280 | | | | | 285 | | | |

| Met | Val | Thr | Val | Val | Gly | Glu | Val | Pro | Leu | Gly | Thr | Ala | Glu | Arg | Val |
| | 290 | | | | | 295 | | | | | 300 | | | | |

| Ala | Leu | Ser | Ile | Arg | Pro | Glu | Ala | Ala | Ala | Gln | Lys |
| 305 | | | | | 310 | | | | | 315 | |

( 2 ) INFORMATION FOR SEQ ID NO:19:

( i ) SEQUENCE CHARACTERISTICS:
      ( A ) LENGTH: 193 amino acids
      ( B ) TYPE: amino acid
      ( C ) STRANDEDNESS: single
      ( D ) TOPOLOGY: linear -continued (ii) MOLECULE TYPE: peptide (xi) SEQUENCE DESCRIPTION: SEQ ID NO:19:

| Met | Leu | Thr | Gln | Glu | Gln | Asp | Gln | Gln | Leu | Val | Glu | Arg | Val | Gln | Arg |
| 1 | | | | 5 | | | | | 10 | | | | | 15 | |
| Gly | Asp | Lys | Arg | Ala | Phe | Asp | Leu | Leu | Val | Leu | Lys | Tyr | Gln | His | Lys |
| | | | 20 | | | | | 25 | | | | | 30 | | |
| Ile | Leu | Gly | Leu | Ile | Val | Arg | Phe | Val | His | Asp | Ala | Gln | Glu | Ala | Gln |
| | | 35 | | | | | 40 | | | | | 45 | | | |
| Asp | Val | Ala | Gln | Glu | Ala | Phe | Ile | Lys | Ala | Tyr | Arg | Ala | Leu | Gly | Asn |
| | 50 | | | | | 55 | | | | | 60 | | | | |
| Phe | Arg | Gly | Asp | Ser | Ala | Phe | Tyr | Thr | Trp | Leu | Tyr | Arg | Ile | Ala | Ile |
| 65 | | | | | 70 | | | | | 75 | | | | | 80 |
| Asn | Thr | Ala | Lys | Asn | His | Leu | Val | Ala | Arg | Gly | Arg | Arg | Pro | Pro | Asp |
| | | | | 85 | | | | | 90 | | | | | 95 | |
| Ser | Asp | Val | Thr | Ala | Glu | Asp | Ala | Glu | Phe | Phe | Glu | Gly | Asp | His | Ala |
| | | | 100 | | | | | 105 | | | | | 110 | | |
| Leu | Lys | Asp | Ile | Glu | Ser | Pro | Glu | Arg | Ala | Met | Leu | Arg | Asp | Glu | Ile |
| | | 115 | | | | | 120 | | | | | 125 | | | |
| Glu | Ala | Thr | Val | His | Gln | Thr | Ile | Gln | Gln | Leu | Pro | Glu | Asp | Leu | Arg |
| | 130 | | | | | 135 | | | | | 140 | | | | |
| Thr | Ala | Leu | Thr | Leu | Arg | Glu | Phe | Glu | Gly | Leu | Ser | Tyr | Glu | Asp | Ile |
| 145 | | | | | 150 | | | | | 155 | | | | | 160 |
| Ala | Thr | Val | Met | Gln | Cys | Pro | Val | Gly | Thr | Val | Arg | Ser | Arg | Ile | Phe |
| | | | | 165 | | | | | 170 | | | | | 175 | |
| Arg | Ala | Arg | Glu | Ala | Ile | Asp | Lys | Ala | Leu | Gln | Pro | Leu | Leu | Arg | Glu |
| | | | 180 | | | | | 185 | | | | | 190 | | |
| Ala | | | | | | | | | | | | | | | |